US012778944B2

(12) United States Patent
Bailey et al.

(10) Patent No.: US 12,778,944 B2
(45) **Date of Patent: *Nov. 3, 2026**

(54) USE OF TIVOZANIB TO TREAT SUBJECTS WITH REFRACTORY CANCER

(71) Applicant: AVEO Pharmaceuticals, Inc., Boston, MA (US)

(72) Inventors: Michael P. Bailey, Boston, MA (US); Michael N. Needle, Boston, MA (US)

(73) Assignee: AVEO Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/376,086

(22) Filed: Oct. 31, 2025

(65) Prior Publication Data

US 2026/0053791 A1 Feb. 26, 2026

Related U.S. Application Data

(63) Continuation of application No. 18/948,852, filed on Nov. 15, 2024, which is a continuation of application No. 17/289,913, filed as application No. PCT/US2019/059904 on Nov. 5, 2019, now abandoned.

(60) Provisional application No. 62/756,033, filed on Nov. 5, 2018.

(51) Int. Cl.

| | |
|---|---|
| ***A61P 35/00*** | (2006.01) |
| ***A61K 9/00*** | (2006.01) |
| ***A61K 31/44*** | (2006.01) |
| ***A61K 31/4545*** | (2006.01) |
| ***A61K 31/4709*** | (2006.01) |
| ***A61K 31/496*** | (2006.01) |
| ***A61P 35/04*** | (2006.01) |
| *A61K 31/4439* | (2006.01) |
| *A61K 31/47* | (2006.01) |
| *A61K 31/506* | (2006.01) |
| *A61K 31/517* | (2006.01) |
| *A61K 39/395* | (2006.01) |

(52) U.S. Cl.

CPC ........ *A61K 31/4709* (2013.01); *A61K 9/0053* (2013.01); *A61K 31/44* (2013.01); *A61K 31/4545* (2013.01); *A61K 31/496* (2013.01); *A61P 35/00* (2018.01); *A61K 31/4439* (2013.01); *A61K 31/47* (2013.01); *A61K 31/506* (2013.01); *A61K 31/517* (2013.01); *A61K 39/3955* (2013.01)

(58) Field of Classification Search

CPC ....... A61P 35/00; A61P 35/04; A61K 31/4709

See application file for complete search history.

(56) References Cited

U.S. PATENT DOCUMENTS

| | | | |
|---|---|---|---|
| 6,187,926 | B1 | 2/2001 | Osawa et al. |
| 6,821,987 | B2 | 11/2004 | Kubo et al. |
| 7,166,722 | B2 | 1/2007 | Matsunaga et al. |
| 7,736,861 | B1 | 6/2010 | Lin et al. |
| 11,504,365 | B2 | 11/2022 | Bailey et al. |
| 2017/0088626 | A1 | 3/2017 | Jure-Kunkel et al. |
| 2017/0166641 | A1 | 6/2017 | Martini et al. |
| 2022/0000858 | A1 | 1/2022 | Bailey et al. |
| 2025/0275955 | A1 | 9/2025 | Bailey et al. |

FOREIGN PATENT DOCUMENTS

| | | | |
|---|---|---|---|
| WO | WO-2011/060162 | A1 | 5/2011 |
| WO | WO-2015/134605 | A1 | 9/2015 |

OTHER PUBLICATIONS

Cowey et al. Drug Design, Development and Therapy (2013); 7:519-527 (Year: 2013).*

Barata et al. Br. J. Cancer. May 24, 2018;119(2):160-163. doi: 10.1038/s41416-018-0104-z. (Year: 2018).*

"A Phase 3, Randomized, Controlled, Multi-Center, Open-Label Study to Compare Tivozanib Hydrochloride to Sorafenib in Subjects With Refractory Advanced Renal Cell Carcinoma," published Oct. 1, 2018 (111 pages).

"A Single-Dose Study of Tivozanib in Subjects With Hepatic Impairment and Normal Hepatic Function," Clinicaltrials.gov Identifier NCT01631097, posted to www.clinicaltrials.gov <http://www.clinicaltrials.gov> on Jun. 27, 2012 (9 pages).

"A Study to Compare Tivozanib (AV-951) to Sorafenib in Subjects With Advanced Renal Cell Carcinoma (TIVO-1)," ClinicalTrials.gov Identifier NCT01030783, posted to www.clinicaltrials.gov <http://www.clinicaltrials.gov> on Dec. 10, 2009 (5 pages).

"A Study to Compare Tivozanib Hydrochloride to Sorafenib in Subjects With Refractory Advanced RCC," ClinicalTrials.gov Identifier NCT02627963, posted to www.clinicaltrials.gov <http://www.clinicaltrials.gov> on Dec. 10, 2015 (4 pages).

"A Study to Compare Tivozanib Hydrochloride to Sorafenib in Subjects With Refractory Advanced RCC," ClinicalTrials.gov Identifier NCT02627963, Aug. 7, 2018, Retrieved from the Internet on Jun. 14, 2022 (12 pages).

(Continued)

*Primary Examiner* — James H Alstrum-Acevedo

*Assistant Examiner* — Chris E Simmons

(74) *Attorney, Agent, or Firm* — MORGAN, LEWIS & BOCKIUS LLP

(57) ABSTRACT

Disclosed is a method of treating cancer, e.g., refractory cancer, with tivozanib. The methods disclosed include, for example, administering tivozanib as a second or third-line therapy to subjects suffering from refractory advanced renal cell carcinoma where traditional therapies as well as more recent targeted and immune-oncology therapies have not adequately treated the subject.

6 Claims, 18 Drawing Sheets

(56) References Cited

OTHER PUBLICATIONS

Agulnik, M. et al., "A phase II study of tivozanib in patients with metastatic and nonresectable soft-tissue sarcomas," Annals of Oncology, 2017, vol. 28, pp. 121-127.
Albiges, L. et al., "TiNivo: A Phase 1b Dose Escalation Trial of Tivozanib and Nivolumab in Renal Cell Carcinoma," Presented at Sixteenth International Kidney Cancer Symposium, Nov. 3-4, 2017.
Aveo Oncology Press Release dated May 26, 2016, entitled "AVEO Announces Dosing of First Patient in the Pivotal Phase 3 TIVO-3 Study of Tivozanib in Renal Cell Carcinoma" (2 pages).
Aveo Oncology Press Release dated Oct. 1, 2018, entitled "AVEO Oncology Announces Initiation of Topline Analysis of Phase 3 TIVO-3 Trial" (2 pages).
Aveo Oncology Press Release dated Nov. 5, 2018, entitled "AVEO Oncology Announces Phase 3 TIVO-3 Trial of Tivozanib in Renal Cell Carcinoma Meets Primary Endpoint" (3 pages).
Aveo Oncology Press Release dated Sep. 10, 2019 entitled "AVEO Oncology Announces Updated Overall Survival Hazard Ratio of 0.99 in Phase 3 TIVO-3 Trial of Tivozanib in Renal Cell Carcinoma" (3 pages).
Aveo Oncology Press Release dated Mar. 10, 2021, entitled "AVEO Oncology Announces U.S. FDA Approval of FOTIVDAR® (tivozanib) for the Treatment of Adult Patients with Relapsed or Refractory Advanced Renal Cell Carcinoma" (3 pages).
Aveo Oncology Press Release dated Jun. 21, 2022, entitled "AVEO Oncology Announces Updated NCCN Clinical Practice Guidelines Elevate FOTIVDAR® (tivozanib) to Category 1 Treatment for Relapsed or Refractory Advanced (R/R) Renal Cell Carcinoma (RCC) Patients" (11 pages).
Barthelemy, P. et al., "TiNivo—tivozanib combined with nivolumab: Safety and efficacy in patients with metastatic renal cell carcinoma (mRCC)," Annals of Oncology, Oct. 2018, vol. 29, Supplement 8, p. viii311, Abstract 878P.
Cella, D. et al., "Treatment benefit of tivozanib hydrochloride versus sorafenib on health-related quality of life (HRQOL) among patients (pts) with advanced/metastatic renal cell carcinoma (mRCC): TIVO-1 study results," Journal of Clinical Oncology, 2013, 31, No. 6_suppl, pp. 355-355; and related poster (1 page) presented Feb. 14-16, 2013, at the American Society of Clinical Oncology Genitourinary Cancers Symposium, Orlando, FL, USA.
Cowey, C. L., "Profile of tivozanib and its potential for the treatment of advanced renal cell carcinoma," Drug Design, Development and Therapy, 2013, 7, pp. 519-527.
Escudier, B. et al., "The role of tivozanib in advanced renal cell carcinoma therapy," Expert Review of Anticancer Therapy, 2018, vol. 18, No. 11, pp. 1113-1124. doi: 10.1080/14737140.2018.1508348. Epub Aug. 21, 2018. PMID: 30084668.
European Medicines Agency Committee for Medicinal Products for Human Use (CHMP) Assessment Report for FOTIVDA (tivozanib) dated Jun. 22, 2017 (123 pages).
European Medicines Agency, Fotivda: EPAR—Product Information, Summary of Product Characteristics, published Nov. 22, 2017.
Eusa Pharma UK, Fotivda 890 mcg hard capsules—Summary of Product Characteristics. Accessed at <https://www.medicines.org.uk/emc/product/8996/smpc> and published Feb. 15, 2018.
Fishman, M. N. et al., "Phase Ib study of tivozanib (AV-951) in combination with temsirolimus in patients with renal cell carcinoma," European Journal of Cancer, 2013, 49, pp. 2841-2850.
Heng, D. Y. C. et al., "External validation and comparison with other models of the International Metastatic Renal-Cell Carcinoma Database Consortium prognostic model: a population-based study," The Lancet Oncology, 2013, vol. 14, pp. 141-148.
Hutson, T. E. et al., "Subgroup analyses of a phase III trial comparing tivozanib hydrochloride versus sorafenib as initial targeted therapy for patients (pts) with metastatic renal cell carcinoma (mRCC)," Journal of Clinical Oncology, 2013, vol. 31, issue 6_suppl, p. 354-354; and related poster presented at the American Society of Clinical Oncology Genitourinary Cancers Symposium, Feb. 14-16, 2013, Orlando, FL USA (1 page).
Hutson, T. et al., "Tivozanib vs sorafenib targeted therapy for advanced renal cell carcinoma: Final results of a phase III trial (901) and efficacy results of a 2nd line tivozanib extension study (902)," Journal of Clinical Oncology, 2015, vol. 33, issue 15_suppl, p. 4557-4557; and related poster (1 page) presented at the Annual Meeting of the American Society of Clinical Oncology (ASCO), May 29-Jun. 2, 2015, Chicago, IL, USA.
International Search Report of the International Searching Authority (ISA/AU) for International Patent Application No. PCT/US2019/059904 dated Mar. 11, 2020 (6 pages).
Lee, S. et al., "Phase 1b/2 study of tivozanib in patients with advanced inoperable hepatocellular carcinoma," Poster Presentation made at American Society of Clinical Oncology Gastrointestinal Cancers Symposium in San Francisco, CA, Jan. 19, 2018 (1 page).
Molina, A. M. et al., "Efficacy of tivozanib treatment after sorafenib in patients with advanced renal cell carcinoma: crossover of a phase 3 study," European Journal of Cancer, Mar. 2018, vol. 94, pp. 87-94.
Motzer, R. et al., "Efficacy and safety data from patients with advanced renal cell cancer treated with tivozanib hydrochloride after progression on sorafenib," Poster No. 364, presented at The American Society of Clinical Oncology Genitourinary Cancers Symposium, Feb. 14-16, 2013, Orlando, FL, USA (1 page).
Motzer, R. J. et al., "Overall survival results from a phase III study of tivozanib hydrocholoride versus sorafenib in patients with renal cell carcinoma," Journal of Clinical Oncology, 2013, 31, No. 6_suppl, p. 350-350; and related poster (1 page) presented at the American Society of Clinical Oncology Genitourinary Cancers Symposium, Feb. 14-16, 2013, Orlando, FL, USA.
Motzer, R.J. et al., "Tivozanib Versus Sorafenib As Initial Targeted Therapy for Patients With Metastatic Renal Cell Carcinoma: Results From a Phase III Trial," Journal of Clinical Oncology, 2013, vol. 31, No. 30, pp. 3791-3800.
Nakamura, K. et al., "KRN951, a Highly Potent Inhibitor of Vascular Endothelial Growth Factor Receptor Tyrosine Kinases, Has Antitumor Activities and Affects Functional Vascular Properties," Cancer Research, 2006, 66(18), pp. 9134-9142.
Neufeld, G. et al., "Vascular endothelial growth factor (VEGF) and its receptors," The FASEB Journal, 1999, vol. 13, pp. 9-22.
Nosov, D. A. et al., "Antitumor activity and safety of tivozanib (AV-951) in a phase II randomized discontinuation trial in patients with renal cell carcinoma," J. Clin. Oncol., 2012, 30(14), pp. 1678-1685. doi: 10.1200/JCO.2011.35.3524. Epub Apr. 9, 2012. PMID: 22493422 (16 pages).
Porta, C. et al., "TIVO-3: Subgroup analysis of progression-free survival of tivozanib compared to sorafenib in subjects with refractory advanced renal cell carcinoma (RCC)," Journal of Clinical Oncology, May 26, 2019, 37, No. 15_suppl, p. 4572-4572; and related poster (1 page) presented at the American Society of Clinical Oncology Annual Meeting, May 31-Jun. 4, 2019, Chicago, IL, USA.
Rini, B. I. et al., "Tivo-3: A phase 3, randomized, controlled, multi-center, open-label study to compare tivozanib hydrochloride to sorafenib in subjects with refractory advanced renal cell carcinoma (RCC)," Journal of Clinical Oncology, published online May 30, 2017, vol. 35, No. 15_suppl, TPS4600; and related poster (1 pg.) presented at the American Society of Clinical Oncology Annual Meeting, Jun. 2-6, 2017, Chicago, IL, USA.
Rini, B. I. et al., "TIVO-3: A phase III, randomized, controlled, multicenter, open-label study to compare tivozanib to sorafenib in subjects with refractory advanced renal cell carcinoma (RCC)," Journal of Clinical Oncology, 2019, vol. 37, issue 7_suppl, 541-541.
Rini, B. I. et al., "TIVO-3: A Phase 3, Randomized, Controlled, Multi-Center, Open-Label Study to Compare Tivozanib to Sorafenib in Subjects with Refractory Advanced Renal Cell Carcinoma (RCC)," slide presentation dated Feb. 16, 2019 (17 pages).
Santoni, M. et al., "Tivozanib for the treatment of renal cell carcinoma," Expert Opinion on Pharmacotherapy, 2018, vol. 19, No. 9, pp. 1021-1025.
Shah, R. R. et al., "Hepatotoxicity of Tyrosine Kinase Inhibitors: Clinical and Regulatory Perspectives," Drug Saf, 2013, vol. 36, pp. 491-503.

(56) References Cited

OTHER PUBLICATIONS

Vermassen, T. et al., "Therapeutic approaches in clear cell and non-clear cell renal cell carcinoma," Acta Clinica Belgica, 2017, vol. 72, No. 1, pp. 12-18.
Wolpin, B. M. et al., "Multicenter Phase II Study of Tivozanib (AV-951) and Everolimus (RAD001) for Patients With Refractory, Metastatic Colorectal Cancer," The Oncologist, 2013, vol. 18, pp. 377-378.
Written Opinion of International Searching Authority (ISA/AU) for International Patent Application No. PCT/US2019/059904 dated Mar. 11, 2020 (9 pages).
U.S. FDA, Cabometyx® (cabozantinib) Prescribing Information, Dec. 2017 (26 pages).
U.S. FDA, Inlyta® (axitinib) Prescribing Information, Aug. 2018 (19 pages).
U.S. FDA, Votrient® (pazopanib) Prescribing Information, May 2017 (28 pages).
U.S. FDA Press Release dated Mar. 10, 2021, entitled "FDA approves tivozanib for relapsed or refractory advanced renal cell carcinoma."
"A Study of Tivozanib (AV-951), an Oral VEGF Receptor Tyrosine Kinase Inhibitor, in the Treatment of Renal Cell Carcinoma," Clinicaltrials.gov Identifier NCT00502307, submitted to www.clinicaltrials.gov <http://www.clinicaltrials.gov> on Oct. 2, 2012 (5 pages).
Aveo Oncology Press Release dated Jun. 20, 2017, entitled "AVEO Oncology Announces Pivotal Phase 3 TIVO-3 Study of Tivozanib in Renal Cell Carcinoma Reaches Enrollment Target" (3 pages).
Aveo Oncology Press Release dated Sep. 20, 2017, entitled "AVEO Oncology and EUSA Pharma Announce TiNivo Combination Study Opt-In" (9 pages).
Bukowski, R. M. et al., "Third generation tyrosine kinase inhibitors and their development in advanced renal cell carcinoma," Frontiers in Oncology, 2012, vol. 2, article 13.
Eskens, F. A.I.m et al., "Abstract LB-201: Updated results from a Phase I study of AV-951 (KRN951), a potent and selective VEGFR-1, -2 and -3 tyrosine kinase inhibitor, in patients with advanced solid tumors," Cancer Research, 2008, 68 (9_Supplement): LB-201.
Hepgur, M. et al., "Tivozanib in the treatment of renal cell carcinoma," Biologics: Targets and Therapy, 2013, vol. 7, pp. 139-148.
Leon, L. et al., "Chapter 18: Side Effects of Targeted Therapy" in *Renal Cell Carcinoma: Molecular Targets and Clinical Applications*, 3rd ed., Bukowski, R. M. et al., eds., Springer Publishing, 2015, pp. 377-416.
Motzer, et al., Tivozanib versus sorafenib as initial targeted therapy for patients with metastatic renal cell carcinoma: Results from a Phase III trial, Protocol Materials (26 pages).
Niwakawa, M. et al., "Phase I study of highly selective inhibitor of VEGFR tyrosine kinase, tivozanib, in Japanese patients with solid tumors," Cancer Science, 2013, vol. 104, No. 8, pp. 1039-1044.
Rini, B. I. et al., "Tivo-3: A phase 3, randomized, controlled, multi-center, open-label study to compare tivozanib hydrochloride to sorafenib in patients with refractory advanced renal cell carcinoma (RCC)," Poster presented at the American Society of Clinical Oncology Annual Meeting, Jun. 2-6, 2017, Chicago, IL, USA (10 pages).
U.S. Department of Health and Human Services, "Common Terminology Criteria for Adverse Events (CTCAE): Version 5.0," published Nov. 27, 2017 (155 pages).
U.S. Department of Health and Human Services, Food and Drug Administration, "Guidance for Industry: Pharmacokinetics in Patients with Impaired Hepatic Function: Study Design, Data Analysis, and Impact on Dosing and Labeling," May 2003 (19 pages).
U.S. FDA, Inlyta® (axitinib) Prescribing Information, Aug. 2014 (21 pages).

* cited by examiner

Kaplan-Meier Analysis of IRR Progression Free Survival Stratified by IMDC Risk and Prior Therapy
(As Randomized)
(ITT Population)

Kaplan-Meier Analysis of Overall Survival
(ITT Population)

FIGURE 3

IRR Best Overall Response with Confirmation (RECIST 1.1 Criteria)
(ITT Population)

| | Tivozanib (N=175) | Sorafenib (N=175) | Total (N=350) |
|---|---|---|---|
| Number of Patients with Measurable Disease at Baseline | 172 | 175 | 347 |
| Best Overall Response, n (%) | | | |
| Complete Response (CR) | 0 | 0 | 0 |
| Partial Response (PR) | 31 (18.0) | 14 (8.0) | 45 (13.0) |
| Stable Disease (SD) | 94 (54.7) | 99 (56.6) | 193 (55.6) |
| Progressive Disease (PD) | 37 (21.5) | 32 (18.3) | 69 (19.9) |
| Not Evaluable (NE) | 3 (1.7) | 5 (2.9) | 8 (2.3) |
| Not Assessed/Not Applicable [1] | 7 (4.1) | 25 (14.3) | 32 (9.2) |
| Objective Response Rate | | | |
| CR+PR, n (%) | 31 (18.02) | 14 (8.00) | 45 (12.97) |
| 95% CI | (12.36, 24.19) | (4.44, 13.06) | |
| Cochran-Mantel-Haenszel p-value | 0.0168 | | |

Abbreviations: ITT = Intent-to-Treat; IRR = Independent Radiological Review; CI = Confidence Interval; RECIST = Response Evaluation Criteria in Solid Tumors.
Percentages are calculated using a denominator of all patients with measurable disease at baseline.
[1] These patients did not have any post-baseline tumor assessments and such it was unable to determine best overall response with confirmation following RECIST v1.1 guidelines.

FIGURE 4

Kaplan-Meier Analysis of IRR Progression Free Survival unstratified (ITT Population)

| | Tivozanib (N=175) | Sorafenib (N=175) | Total (N=350) |
|---|---|---|---|
| Status, n (%) | | | |
| Events Observed | 123 (70.3) | 123 (70.3) | 246 (70.3) |
| Progressive Disease Event | 103 (58.9) | 109 (62.3) | 212 (60.6) |
| Death Event | 20 (11.4) | 14 (8.0) | 34 (9.7) |
| Censored | 52 (29.7) | 52 (29.7) | 104 (29.7) |
| PFS | | | |
| Quartiles (95% CI) | | | |
| 25% | 2.27 ( 1.87, 3.61) | 2.23 ( 1.91, 3.61) | 2.27 ( 1.94, 3.58) |
| 50% | 5.59 ( 5.29, 7.33) | 3.88 ( 3.71, 5.55) | 5.49 ( 3.91, 5.62) |
| 75% | 14.62 (11.04, - ) | 7.46 ( 7.33, 9.23) | 10.97 ( 9.13, 12.88) |
| Survival Probabilities (95% CI) | | | |
| 1 Year | 0.28 ( 0.20, 0.35) | 0.11 ( 0.05, 0.17) | 0.20 ( 0.15, 0.25) |
| 2 Years | 0.18 ( 0.11, 0.25) | 0.05 ( 0.01, 0.09) | 0.12 ( 0.08, 0.17) |
| Hazard Ratio [1] | | 0.67 | |
| 95% CI | | ( 0.52, 0.86) | |
| Unstratified Log-rank p-value [2] | | 0.0019 | |

Abbreviations: ITT = Intent-to-Treat; IRR = Independent Radiological Review; PFS = Progression Free Survival; CI = Confidence Interval; IMDC = International Metastatic Renal Cell Carcinoma Database Consortium; VEGFR = Vascular Endothelial Growth Factor Receptor; TKI = Tyrosine Kinase Inhibitor.
[1] Hazard Ratio is based on a Cox proportional hazards model with Sorafenib as the reference group. [2] p-value is based on the log-rank test.

FIGURE 5

Kaplan-Meier Analysis of IRR Progression Free Survival subset by Prior Check Point Inhibitor: Yes (ITT Population)

| | Tivozanib (N=52) | Sorafenib (N=46) | Total (N=98) |
|---|---|---|---|
| Status, n (%) | | | |
| Events Observed | 31 (59.6) | 25 (54.3) | 56 (57.1) |
| Progressive Disease Event | 26 (50.0) | 22 (47.8) | 48 (49.0) |
| Death Event | 5 (9.6) | 3 (6.5) | 8 (8.2) |
| Censored | 21 (40.4) | 21 (45.7) | 42 (42.9) |
| PFS | | | |
| Quartiles (95% CI) | | | |
| 25% | 3.75 ( 1.84, 5.42) | 2.43 ( 2.00, 3.06) | 3.55 ( 2.04, 4.11) |
| 50% | 7.29 ( 5.29, 13.08) | 5.91 ( 3.58, 7.46) | 6.01 ( 5.29, 8.51) |
| 75% | (11.07, - ) | 9.43 ( 6.01, 11.20) | 13.08 ( 9.30, - ) |
| Survival Probabilities (95% CI) | | | |
| 1 Year | 0.37 ( 0.22, 0.51) | 0.05 ( 0.00, 0.14) | 0.25 ( 0.15, 0.36) |
| 2 Years | 0.28 ( 0.12, 0.44) | ( - , - ) | 0.19 ( 0.08, 0.30) |
| Hazard Ratio [1] | | 0.60 | |
| 95% CI | | ( 0.35, 1.03) | |
| Unstratified Log-rank p-value [2] | | 0.0616 | |

Abbreviations: ITT = Intent-to-Treat; IRR = Independent Radiological Review; PFS = Progression Free Survival; CI = Confidence Interval.

[1] Hazard Ratio is based on a Cox proportional hazards model with Sorafenib as the reference group. [2] p-value is based on the log-rank test.

FIGURE 6

Kaplan-Meier Analysis of IRR Progression Free Survival stratified by IMDC Risk Category and Prior Therapy (As Randomized) (ITT Population)

| | Tivozanib (N=175) | Sorafenib (N=175) | Total (N=350) |
|---|---|---|---|
| Status, n (%) | | | |
| Events Observed | 123 (70.3) | 123 (70.3) | 246 (70.3) |
| Progressive Disease Event | 103 (58.9) | 109 (62.3) | 212 (60.6) |
| Death Event | 20 (11.4) | 14 (8.0) | 34 (9.7) |
| Censored | 52 (29.7) | 52 (29.7) | 104 (29.7) |
| Status - IMDC: Favorable, n (%) | | | |
| Events Observed | 21 (12.0) | 22 (12.6) | 43 (12.3) |
| Progressive Disease Event | 20 (11.4) | 21 (12.0) | 41 (11.7) |
| Death Event | 1 (0.6) | 1 (0.6) | 2 (0.6) |
| Censored | 13 (7.4) | 14 (8.0) | 27 (7.7) |
| Status - IMDC: Intermediate, n (%) | | | |
| Events Observed | 73 (41.7) | 74 (42.3) | 147 (42.0) |
| Progressive Disease Event | 58 (33.1) | 66 (37.7) | 124 (35.4) |
| Death Event | 15 (8.6) | 8 (4.6) | 23 (6.6) |
| Censored | 36 (20.6) | 31 (17.7) | 67 (19.1) |
| Status - IMDC: Poor, n (%) | | | |
| Events Observed | 29 (16.6) | 27 (15.4) | 56 (16.0) |
| Progressive Disease Event | 25 (14.3) | 22 (12.6) | 47 (13.4) |
| Death Event | 4 (2.3) | 5 (2.9) | 9 (2.6) |
| Censored | 3 (1.7) | 7 (4.0) | 10 (2.9) |
| Status - Prior Therapy: 2 VEGFR TKIs, n (%) | | | |
| Events Observed | 56 (32.0) | 61 (34.9) | 117 (33.4) |
| Progressive Disease Event | 47 (26.9) | 53 (30.3) | 100 (28.6) |
| Death Event | 9 (5.1) | 8 (4.6) | 17 (4.9) |
| Censored | 23 (13.1) | 19 (10.9) | 42 (12.0) |
| Status - Prior Therapy: Checkpoint Inhibitor + VEGFR TKI, n (%) | | | |
| Events Observed | 29 (16.6) | 27 (15.4) | 56 (16.0) |
| Progressive Disease Event | 24 (13.7) | 23 (13.1) | 47 (13.4) |
| Death Event | 5 (2.9) | 4 (2.3) | 9 (2.6) |
| Censored | 18 (10.3) | 17 (9.7) | 35 (10.0) |

FIGURE 6 (continued)

| | Tivozanib (N=175) | Sorafenib (N=175) | Total (N=350) |
|---|---|---|---|
| Status - Prior Therapy: Other + VEGFR TKI, n (%) | | | |
| Events Observed | 38 (21.7) | 35 (20.0) | 73 (20.9) |
| Progressive Disease Event | 32 (18.3) | 33 (18.9) | 65 (18.6) |
| Death Event | 6 (3.4) | 2 (1.1) | 8 (2.3) |
| Censored | 11 (6.3) | 16 (9.1) | 27 (7.7) |
| | | | |
| PFS | | | |
| Quartiles (95% CI) | | | |
| 25% | 2.27 ( 1.87, 3.61) | 2.23 ( 1.91, 3.61) | 2.27 ( 1.94, 3.58) |
| 50% | 5.59 ( 5.29, 7.33) | 3.88 ( 3.71, 5.55) | 5.49 ( 3.91, 5.62) |
| 75% | 14.62 (11.04, - ) | 7.46 ( 7.33, 9.23) | 10.97 ( 9.13, 12.88) |
| | | | |
| Survival Probabilities (95% CI) | | | |
| 1 Year | 0.28 ( 0.20, 0.35) | 0.11 ( 0.05, 0.17) | 0.20 ( 0.15, 0.25) |
| 2 Years | 0.18 ( 0.11, 0.25) | 0.05 ( 0.01, 0.09) | 0.12 ( 0.08, 0.17) |
| | | | |
| Hazard Ratio [1] | | 0.73 | |
| 95% CI | | ( 0.56, 0.94) | |
| | | | |
| Stratified Log-rank p-value [2] | | 0.0165 | |

Abbreviations: ITT = Intent-to-Treat; IRR = Independent Radiological Review; PFS = Progression Free Survival; CI = Confidence Interval; IMDC = International Metastatic Renal Cell Carcinoma Database Consortium; VEGFR = Vascular Endothelial Growth Factor Receptor; TKI = Tyrosine Kinase Inhibitor.

[1] Hazard Ratio is based on a stratified Cox proportional hazards model with Sorafenib as the reference group.

[2] p-value is based on the stratified log-rank test. Both tests are stratified by IMDC risk category (favorable vs. intermediate vs. poor) and prior therapy (two prior VEGFR TKIs vs. a prior checkpoint inhibitor plus a prior VEGFR TKI vs. a prior VEGFR TKI plus any other systemic agent) as stratification as randomized factors.

FIGURE 7
Kaplan-Meier Analysis of Overall Survival (ITT Population)

| | Tivozanib (N=175) | Sorafenib (N=175) | Total (N=350) |
|---|---|---|---|
| Status, n (%) | | | |
| Events Observed | 114 (65.1) | 113 (64.6) | 227 (64.9) |
| Censored | 61 (34.9) | 62 (35.4) | 123 (35.1) |
| Status - IMDC: Favorable, n (%) | | | |
| Events Observed | 13 (7.4) | 12 (6.9) | 25 (7.1) |
| Censored | 21 (12.0) | 24 (13.7) | 45 (12.9) |
| Status - IMDC: Intermediate, n (%) | | | |
| Events Observed | 74 (42.3) | 71 (40.6) | 145 (41.4) |
| Censored | 35 (20.0) | 34 (19.4) | 69 (19.7) |
| Status - IMDC: Poor, n (%) | | | |
| Events Observed | 27 (15.4) | 30 (17.1) | 57 (16.3) |
| Censored | 5 (2.9) | 4 (2.3) | 9 (2.6) |
| Status - Prior Therapy: 2 VEGFR TKIs, n (%) | | | |
| Events Observed | 53 (30.3) | 52 (29.7) | 105 (30.0) |
| Censored | 26 (14.9) | 28 (16.0) | 54 (15.4) |
| Status - Prior Therapy: Checkpoint Inhibitor + VEGFR TKI, n (%) | | | |
| Events Observed | 27 (15.4) | 26 (14.9) | 53 (15.1) |
| Censored | 20 (11.4) | 18 (10.3) | 38 (10.9) |
| Status - Prior Therapy: Other + VEGFR TKI, n (%) | | | |
| Events Observed | 34 (19.4) | 35 (20.0) | 69 (19.7) |
| Censored | 15 (8.6) | 16 (9.1) | 31 (8.9) |
| OS (months) | | | |
| Quartiles (95% CI) | | | |
| 25% | 7.39 ( 5.98, 10.18) | 7.33 ( 6.41, 10.87) | 7.33 ( 6.47, 9.59) |
| 50% | 16.39 (13.44, 22.21) | 19.65 (14.95, 24.21) | 17.28 (15.01, 21.68) |
| 75% | (32.82, - ) | (32.43, - ) | (32.95, - ) |
| Survival Probabilities (95% CI) | | | |
| 1 Year | 0.60 ( 0.53, 0.67) | 0.66 ( 0.59, 0.73) | 0.63 ( 0.58, 0.68) |
| 2 Years | 0.40 ( 0.32, 0.47) | 0.43 ( 0.35, 0.50) | 0.41 ( 0.36, 0.46) |

FIGURE 7 (continued)

| | Tivozanib (N=175) | Sorafenib (N=175) | Total (N=350) |
|---|---|---|---|
| Hazard Ratio [1] | | 0.99 | |
| 95% CI | | ( 0.76, 1.29) | |
| Stratified Log-rank p-value [2] | | 0.9501 | |

Abbreviations: ITT = Intent-to-Treat; OS = Overall Survival; CI = Confidence Interval; IMDC = International Metastatic Renal Cell Carcinoma Database Consortium; VEGFR = Vascular Endothelial Growth Factor Receptor; TKI = Tyrosine Kinase Inhibitor.

[1] Hazard Ratio is based on a stratified Cox proportional hazards model with Sorafenib as the reference group.

[2] p-value is based on the stratified log-rank test. Both tests are stratified by IMDC risk category (favorable vs. intermediate vs. poor) and prior therapy (two prior VEGFR TKIs vs. a prior checkpoint inhibitor plus a prior VEGFR TKI vs. a prior VEGFR TKI plus any other systemic agent) as stratification as randomized factors.

FIGURE 8

Kaplan-Meier Analysis of Overall Survival subset by Prior Check Point Inhibitor: Yes (ITT Population)

| | Tivozanib (N=53) | Sorafenib (N=48) | Total (N=101) |
|---|---|---|---|
| Status, n (%) | | | |
| Events Observed | 32 (60.4) | 27 (56.3) | 59 (58.4) |
| Censored | 21 (39.6) | 21 (43.8) | 42 (41.6) |
| OS (months) | | | |
| Quartiles (95% CI) | | | |
| 25% | 10.69 ( 8.51, 13.44) | 11.24 ( 6.01, 17.71) | 11.07 ( 8.71, 13.44) |
| 50% | 20.52 (13.44, 32.82) | 23.00 (14.92, - ) | 22.21 (15.84, 27.76) |
| 75% | (27.76, - ) | (27.56, - ) | (32.82, - ) |
| Survival Probabilities (95% CI) | | | |
| 1 Year | 0.69 ( 0.57, 0.82) | 0.74 ( 0.61, 0.86) | 0.71 ( 0.62, 0.80) |
| 2 Years | 0.44 ( 0.31, 0.58) | 0.49 ( 0.34, 0.64) | 0.46 ( 0.36, 0.56) |
| Hazard Ratio [1] | | 1.06 | |
| 95% CI | | ( 0.63, 1.76) | |
| Unstratified Log-rank p-value [2] | | 0.8360 | |

Abbreviations: ITT = Intent-to-Treat; OS = Overall Survival; CI = Confidence Interval.

[1] Hazard Ratio is based on a Cox proportional hazards model with Sorafenib as the reference group.

[2] p-value is based on the log-rank test.

FIGURE 9

Forest plot of Hazard Ratio with 95% Confidence Interval for Progression Free Survival from Subgroup Analysis (ITT Population)

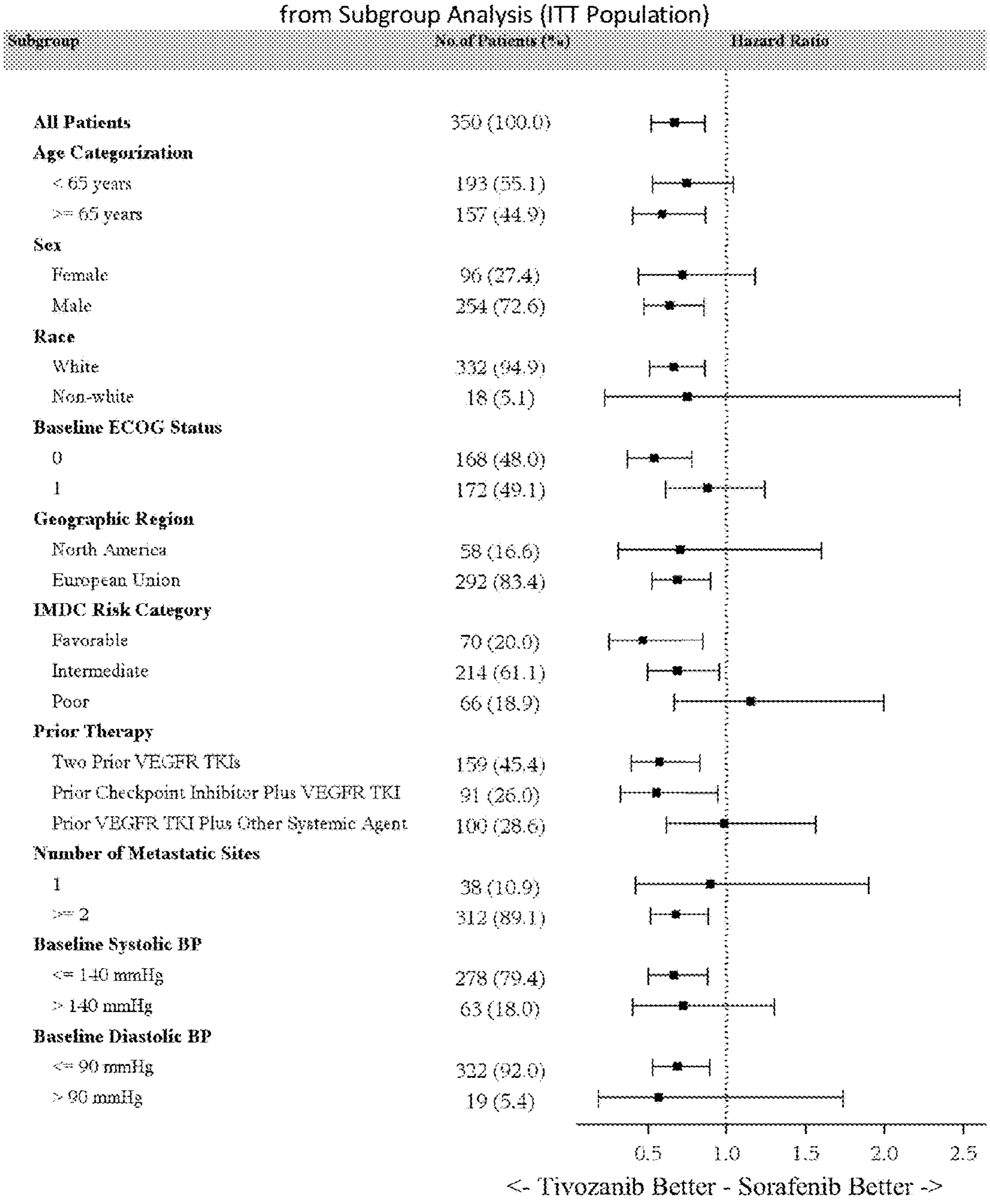

Abbreviations: ITT = Intent-to-Treat; BP = Blood Pressure; IMDC = International Metastatic Renal-Cell Carcinoma Database Consortium; VEGFR = Vascular Endothelial Growth Factor Receptor; TKI = Thyrosine Kinase Inhibitor; ECOG = Eastern Co-operative Oncology Group; mmHg = millimeter of mercury. Note: Hazard Ratio is based on a Cox proportional hazards model with Sorafenib as the reference group. Baseline is the last non-missing measurement before the first dose of study drug.

FIGURE 10
Subgroup Analysis of Progression Free Survival using Cox Model
(ITT Population)

| | Tivozanib (N=175) | | Sorafenib (N=175) | | Tivozanib vs. Sorafenib Cox Model | |
|---|---|---|---|---|---|---|
| | n | No. of Events/Censored | n | No. of Events/Censored | Hazard Ratio [1] | (95% CI) |
| All Patients | 175 | 123/52 | 175 | 123/52 | 0.67 | (0.52, 0.86) |
| Age Categorization | | | | | | |
| < 65 years | 98 | 69/29 | 95 | 68/27 | 0.74 | (0.53, 1.04) |
| >= 65 years | 77 | 54/23 | 80 | 55/25 | 0.59 | (0.40, 0.87) |
| Sex | | | | | | |
| Female | 49 | 36/13 | 47 | 30/17 | 0.72 | (0.44, 1.18) |
| Male | 126 | 87/39 | 128 | 93/35 | 0.64 | (0.47, 0.86) |
| Race | | | | | | |
| White | 165 | 116/49 | 167 | 118/49 | 0.66 | (0.51, 0.86) |
| Non-white | 10 | 7/3 | 8 | 5/3 | 0.75 | (0.23, 2.48) |
| Baseline ECOG Status | | | | | | |
| 0 | 85 | 55/30 | 83 | 60/23 | 0.54 | (0.37, 0.78) |
| 1 | 88 | 68/20 | 84 | 61/23 | 0.87 | (0.62, 1.24) |
| Time from Initial Diagnosis to Randomization | | | | | | |
| < 1 year | 2 | 1/1 | 5 | 3/2 | 0.71 | (0.06, 8.02) |
| >= 1 year | 145 | 102/43 | 139 | 103/36 | 0.67 | (0.51, 0.89) |
| Geographic Region | | | | | | |
| North America | 31 | 17/14 | 27 | 9/18 | 0.71 | (0.31, 1.60) |
| European Union | 144 | 106/38 | 148 | 114/34 | 0.69 | (0.52, 0.90) |
| IMDC Risk Category (as Randomized) | | | | | | |
| Favorable | 34 | 21/13 | 36 | 22/14 | 0.46 | (0.25, 0.85) |
| Intermediate | 109 | 73/36 | 105 | 74/31 | 0.69 | (0.49, 0.95) |
| Poor | 32 | 29/3 | 34 | 27/7 | 1.15 | (0.67, 2.00) |
| Prior Therapy (as Randomized) | | | | | | |
| Two Prior VEGFR TKIs | 79 | 56/23 | 80 | 61/19 | 0.57 | (0.39, 0.83) |
| Prior Checkpoint Inhibitor Plus VEGFR TKI | 47 | 29/18 | 44 | 27/17 | 0.55 | (0.32, 0.94) |
| Prior VEGFR TKI Plus Other Systemic Agent | 49 | 38/11 | 51 | 35/16 | 0.98 | (0.62, 1.56) |

FIGURE 10 (Continued)

| | Tivozanib (N=175) n | Tivozanib (N=175) No. of Events/Censored | Sorafenib (N=175) n | Sorafenib (N=175) No. of Events/Censored | Tivozanib vs. Sorafenib Cox Model Hazard Ratio [1] | (95% CI) |
|---|---|---|---|---|---|---|
| Number of Metastatic Sites | | | | | | |
| 1 | 13 | 11/2 | 25 | 19/6 | 0.89 | (0.42, 1.90) |
| >= 2 | 162 | 112/50 | 150 | 104/46 | 0.68 | (0.52, 0.89) |
| Baseline Systolic BP | | | | | | |
| <= 140 mmHg | 140 | 98/42 | 138 | 100/38 | 0.66 | (0.50, 0.88) |
| > 140 mmHg | 33 | 25/8 | 30 | 21/9 | 0.72 | (0.40, 1.30) |
| Baseline Diastolic BP | | | | | | |
| <= 90 mmHg | 164 | 117/47 | 158 | 114/44 | 0.69 | (0.53, 0.90) |
| > 90 mmHg | 9 | 6/3 | 10 | 7/3 | 0.57 | (0.18, 1.74) |

Abbreviations: ITT = Intent-to-Treat; CI = Confidence Interval; BP = Blood Pressure; IMDC = International Metastatic Renal-Cell Carcinoma Database Consortium; VEGFR = Vascular Endothelial Growth Factor Receptor; TKI = Thyrosine Kinase Inhibitor; ECOG = Eastern Co-operative Oncology Group; mmHg = millimeter of mercury.
[1] Hazard Ratio is based on a Cox proportional hazards model with Sorafenib as the reference group. Sub-group statistics are model-based.
Baseline is the last non-missing measurement before the first dose of study drug.

Forest plot of Hazard Ratio with 95% Confidence Interval for Overall Survival from Subgroup Analysis (ITT Population)

FIGURE 12

Subgroup Analysis of Overall Survival using Cox Model
(ITT Population)

| | Tivozanib (N=175) | | Sorafenib (N=175) | | Tivozanib vs. Sorafenib Cox Model | |
|---|---|---|---|---|---|---|
| | n | No. of Events/Censored | n | No. of Events/Censored | Hazard Ratio [1] | (95% CI) |
| All Patients | 175 | 114/61 | 175 | 113/62 | 1.03 | (0.79, 1.33) |
| Age Categorization | | | | | | |
| < 65 years | 98 | 65/33 | 95 | 65/30 | 1.00 | (0.71, 1.41) |
| >= 65 years | 77 | 49/28 | 80 | 48/32 | 1.06 | (0.71, 1.58) |
| Sex | | | | | | |
| Female | 49 | 30/19 | 47 | 33/14 | 0.87 | (0.53, 1.43) |
| Male | 126 | 84/42 | 128 | 80/48 | 1.10 | (0.81, 1.49) |
| Race | | | | | | |
| White | 165 | 108/57 | 167 | 106/61 | 1.05 | (0.80, 1.37) |
| Non-white | 10 | 6/4 | 8 | 7/1 | 0.73 | (0.24, 2.18) |
| Baseline ECOG Status | | | | | | |
| 0 | 85 | 48/37 | 83 | 47/36 | 1.01 | (0.68, 1.52) |
| 1 | 88 | 65/23 | 84 | 62/22 | 0.99 | (0.70, 1.41) |
| Time from Initial Diagnosis to Randomization | | | | | | |
| < 1 year | 2 | 2/0 | 5 | 5/0 | 1.14 | (0.19, 6.95) |
| >= 1 year | 145 | 97/48 | 139 | 93/46 | 1.01 | (0.76, 1.34) |
| Geographic Region | | | | | | |
| North America | 31 | 15/16 | 27 | 13/14 | 1.01 | (0.48, 2.13) |
| European Union | 144 | 99/45 | 148 | 100/48 | 1.04 | (0.79, 1.38) |
| IMDC Risk Category (as Randomized) | | | | | | |
| Favorable | 34 | 13/21 | 36 | 12/24 | 1.17 | (0.53, 2.58) |
| Intermediate | 109 | 74/35 | 105 | 71/34 | 1.08 | (0.78, 1.49) |
| Poor | 32 | 27/5 | 34 | 30/4 | 0.72 | (0.43, 1.21) |

FIGURE 12 (Continued)

| | Tivozanib (N=175) | | Sorafenib (N=175) | | Tivozanib vs. Sorafenib Cox Model | |
|---|---|---|---|---|---|---|
| | n | No. of Events/Censored | n | No. of Events/Censored | Hazard Ratio [1] | (95% CI) |
| Prior Therapy (as Randomized) | | | | | | |
| Two Prior VEGFR TKIs | 79 | 53/26 | 80 | 52/28 | 1.02 | (0.70, 1.50) |
| Prior Checkpoint Inhibitor Plus VEGFR TKI | 47 | 27/20 | 44 | 26/18 | 0.94 | (0.55, 1.60) |
| Prior VEGFR TKI Plus Other Systemic Agent | 49 | 34/15 | 51 | 35/16 | 1.14 | (0.71, 1.82) |
| Number of Metastatic Sites | | | | | | |
| 1 | 12 | 9/3 | 23 | 13/10 | 1.92 | (0.81, 4.54) |
| >= 2 | 163 | 105/58 | 152 | 100/52 | 0.96 | (0.73, 1.26) |
| Baseline Systolic BP | | | | | | |
| <= 140 mmHg | 140 | 90/50 | 138 | 93/45 | 0.92 | (0.69, 1.24) |
| > 140 mmHg | 33 | 23/10 | 30 | 17/13 | 1.46 | (0.78, 2.75) |
| Baseline Diastolic BP | | | | | | |
| <= 90 mmHg | 164 | 108/56 | 158 | 106/52 | 0.99 | (0.75, 1.29) |
| > 90 mmHg | 9 | 5/4 | 10 | 4/6 | 1.45 | (0.38, 5.50) |

Abbreviations: ITT = Intent-to-Treat; CI = Confidence Interval; BP = Blood Pressure; IMDC = International Metastatic Renal-Cell Carcinoma Database Consortium; VEGFR = Vascular Endothelial Growth Factor Receptor; TKI = Thyrosine Kinase Inhibitor; ECOG = Eastern Co-operative Oncology Group; mmHg = millimeter of mercury.
[1] Hazard Ratio is based on a Cox proportional hazards model with Sorafenib as the reference group. Sub-group statistics are model-based.
Baseline is the last non-missing measurement before the first dose of study drug.

FIGURE 13

Best Overall Response Rate with Confirm (RECIST 1.1 Criteria) (ITT Population)

Best Overall Response N(%) 95% CI

| | | Tivozanib (N=175) | Sorafenib (N=175) |
|---|---|---|---|
| **All Prior Therapies** | N[%] | 31 (18.0) | 14 (8.0) |
| | 95% CI [%] | (12.6, 24.6) | (4.4, 13.0) |
| | | | |
| TWO PRIOR VEGFR TKIS | N[%] | 12 (15.2) | 6 (7.5) |
| | 95% CI [%] | (8.1, 25.0) | (2.8, 15.6) |
| | | | |
| A PRIOR CHECKPOINT INHIBITOR PLUS A PRIOR VEGFR TKI | N[%] | 11 (24.4) | 3 (6.8) |
| | 95% CI [%] | (12.9, 39.6) | (1.4, 18.7) |
| | | | |
| A PRIOR VEGFR TKI PLUS ANY OTHER SYSTEMIC AGENT | N[%] | 8 (16.7) | 5 (9.8) |
| | 95% CI [%] | (7.5, 30.3) | (3.3, 21.4) |

Footnote: Three Tivozanib subjects excluded due to no measurable disease at baseline.

Footnote: 7 Tivozanib subjects were not assessed; 25 Sorafenib subjects were not assessed.

FIGURE 14

Duration of Response (ITT Population)

| | Tivozanib (N=175) | Sorafenib (N=175) | Total (N=350) |
|---|---|---|---|
| Patients with Objective Response | 31 | 14 | 45 |
| Status, n (%) | | | |
| Events Observed | 10 (32.3) | 9 (64.3) | 19 (42.2) |
| Censored | 21 (67.7) | 5 (35.7) | 26 (57.8) |
| Quartiles (95% CI) | | | |
| 25% | 9.79 ( 3.81, - ) | 5.55 ( 5.55, 5.65) | 5.58 ( 5.55, 12.91) |
| 50% | (12.91, - ) | 5.65 ( 5.55, - ) | 16.59 ( 9.79, - ) |
| 75% | ( - , - ) | ( 5.65, - ) | ( - , - ) |
| Duration of Response Probabilities (95% CI) | | | |
| 1 Year | 0.71 ( 0.53, 0.88) | 0.46 ( 0.19, 0.73) | 0.63 ( 0.48, 0.78) |
| 2 Years | 0.55 ( 0.31, 0.79) | ( - , - ) | 0.46 ( 0.27, 0.64) |

Abbreviations: ITT = Intent-to-Treat; IRR = Independent Radiological Review; CI = Confidence Interval; IMDC = International Metastatic Renal Cell Carcinoma Database Consortium; VEGFR = Vascular Endothelial Growth Factor Receptor;
TKI = Tyrosine Kinase Inhibitor.
[1] Hazard Ratio is based on a stratified Cox proportional hazards model with Sorafenib as the reference group. [2] p-value is based on the stratified log-rank test. Both tests are stratified by IMDC risk category (favorable vs. intermediate vs. poor) and prior therapy (two prior VEGFR TKIs vs. a prior checkpoint inhibitor plus a prior VEGFR TKI vs. a prior VEGFR TKI plus any other systemic agent) as stratification as randomized factors.
Percentages are calculated based on patients with objective response.

USE OF TIVOZANIB TO TREAT SUBJECTS WITH REFRACTORY CANCER

CROSS-REFERENCE TO RELATED APPLICATIONS

This application is a continuation of U.S. patent application Ser. No. 18/948,852, filed Nov. 15, 2024, which is a continuation of U.S. patent application Ser. No. 17/289,913, filed Apr. 29, 2021, which is a U.S. National Stage Application filed under 35 U.S.C. § 371 of International Patent Application No. PCT/US2019/059904, filed Nov. 5, 2019, which claims priority to and the benefit of U.S. Provisional Patent Application No. 62/756,033, filed Nov. 5, 2018; the contents of each of which are incorporated by reference herein in their entirety.

FIELD OF THE INVENTION

The field of the invention is medicine, oncology, tyrosine kinase inhibitors, VEGF receptor inhibitors, and pharmaceuticals.

BACKGROUND

Tivozanib (previously known as AV-951 and KRN951) is a potent and selective small-molecule inhibitor of vascular endothelial growth factor (VEGF) receptor tyrosine kinase inhibitor (VEGF TKI) that has demonstrated significant anti-tumor effects in pre-clinical experiments. (Nakamura et al., 2006, Cancer Res. 66:9134-9142).

Tivozanib inhibits phosphorylation of VEGF receptors (VEGFR) −1, −2 and −3 at picomolar concentrations ($IC_{50}$ of 0.21, 0.16 and 0.24 nM respectively), and inhibits c-Kit and platelet derived growth factor receptor (PDGFR) at 10-times higher concentrations ($IC_{50}$ of 1.63 and 1.72 nM respectively).

Based on its biochemical profile, tivozanib appears to be one of the most potent and selective VEGF tyrosine kinase inhibitors in clinical development. Other agents used for treatment of renal cell carcinoma (RCC) such as sunitinib and sorafenib inhibit multiple tyrosine kinases in addition to the VEGF receptor tyrosine kinase, leading to off-target toxicities such as fatigue, hand-foot syndrome, stomatitis, and neutropenia. However, the adverse event (AE) profile of tivozanib demonstrates that it is a selective VEGF tyrosine kinase inhibitor, with minimal off-target toxicities. In a prior phase III clinical trial comparing tivozanib and sorafenib, tivozanib had fewer treatment interruptions and dose reductions due to AEs. (Motzer et al. (2013), J. Clinical Oncology, 31:3791-3799).

Approximately 208,500 new cases of kidney cancer are diagnosed in the world each year, of which 40,000 new cases are diagnosed in North America and 63,300 new cases in the European Union (EU). Renal cell carcinoma accounts for 80%-85% of all malignant kidney tumors. Advanced RCC is highly resistant to chemotherapy, and interleukin-2 and interferon-α have low levels of anti-tumor activity. Recently, drugs that block the VEGF pathway such as sunitinib, sorafenib, bevacizumab, pazopanib, and axitinib have demonstrated significant anti-tumor activity in Phase 3 trials. As a result, these drugs have become the standard of care for the treatment of subjects with advanced RCC.

The various forms of VEGF bind to 3 tyrosine kinase receptors: the vascular endothelial growth factor receptors, VEGFR-1, VEGFR-2, and VEGFR-3 retrospectively. This binding results in phosphorylation of the receptors catalyzed by the protein kinase, and the promotion of a signal transduction cascade. Deregulation of VEGF expression contributes to the progression and spread of solid tumors by promoting tumor angiogenesis (Neufeld et al., (1999), FASEB J., 13:9-22). Tivozanib inhibits VEGFR-associated tyrosine kinase activity and, as a result, may offer a potential therapy for subjects with cancer by controlling tumor growth.

Further, in subjects for whom first and second line therapies against renal cell carcinoma fail, such as sunitinib, sorafenib, bevacizumab, pazopanib, axitinib or checkpoint inhibitors (e.g., PD-1 and PD-L1 inhibitors), there is still a need for additional therapies for treating such subjects.

SUMMARY OF THE INVENTION

The present invention provides improved methods of treating subjects with advanced and refractory cancers, such as renal cell carcinoma. The methods comprise administering to subject in need of such treatment an effective amount or an effective treatment regimen of tivozanib.

In one aspect, the invention provides a method of treating a subject suffering from advanced or refractory cancer wherein the subject has previously been treated with at least one anti-cancer therapy. The method comprises administering to the subject an effective amount or an effective treatment regimen of tivozanib. In one embodiment, the subject suffers from refractory cancer.

In another aspect, the invention provides a method of treating a subject suffering from advanced or refractory renal cell carcinoma wherein the subject has previously been treated with at least one anti-cancer therapy. The method comprises administering to the subject an effective amount or an effective treatment regimen of tivozanib. In one embodiment, the subject suffers from refractory renal cell carcinoma.

In certain embodiments of any of the foregoing methods, the method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle.

In another aspect, the invention provides a method of treating a subject suffering from refractory cancer wherein the subject has previously been treated with at least one anti-cancer therapy. The method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle.

In another aspect, the invention provides a method of treating a subject suffering from refractory renal cell carcinoma wherein the subject has previously been treated with at least one anti-cancer therapy. The method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle.

In certain embodiments of any of the foregoing methods: (a) the subject has previously been treated with at least one checkpoint inhibitor; (b) the subject has previously been treated with at least one vascular endothelial growth factor receptor tyrosine kinase inhibitor (VEGFR TKI); (c) the subject has previously been treated with a vascular endothelial growth factor receptor tyrosine kinase inhibitor (VEGFR TKI) and a checkpoint inhibitor; or (d) the subject has previously been treated with two vascular endothelial growth factor receptor tyrosine kinase inhibitors (VEGFR TKI). For example, in one embodiment, the subject has previously been treated with at least one checkpoint inhibitor. In another embodiment, the subject has previously been treated with at least one vascular endothelial growth factor receptor tyrosine kinase inhibitor (VEGFR TKI). In yet another embodiment, the subject has previously been treated with a vascular endothelial growth factor receptor tyrosine kinase inhibitor (VEGFR TKI) and a checkpoint inhibitor. In a still further embodiment, the subject has previously been treated with two vascular endothelial growth factor receptor tyrosine kinase inhibitors (VEGFR TKI).

In certain embodiments of any of the foregoing methods, the subject has not responded to or has stopped responding to previous treatment with: (a) at least one checkpoint inhibitor; (b) at least one vascular endothelial growth factor receptor tyrosine kinase inhibitor (VEGFR TKI); (c) a vascular endothelial growth factor receptor tyrosine kinase inhibitor (VEGFR TKI) and a checkpoint inhibitor; or (d) two vascular endothelial growth factor receptor tyrosine kinase inhibitors (VEGFR TKI). For example, in one embodiment, the subject has not responded to or has stopped responding to previous treatment with at least one checkpoint inhibitor. In another embodiment, the subject has not responded or has stopped responding to previous treatment with at least one vascular endothelial growth factor receptor tyrosine kinase inhibitor (VEGFR TKI). In yet another embodiment, the subject has not responded to or has stopped responding to previous treatment with a vascular endothelial growth factor receptor tyrosine kinase inhibitor (VEGFR TKI) and a checkpoint inhibitor. In a still further embodiment, the subject has not responded to or has stopped responding to previous treatment with two vascular endothelial growth factor receptor tyrosine kinase inhibitors (VEGFR TKI).

In another aspect, the invention provides a method of treating a subject suffering from renal cell carcinoma (e.g., advanced and/or refractory renal cell carcinoma). The method comprises administering to the subject an effective amount or an effective treatment regimen of tivozanib in combination with a checkpoint inhibitor. In certain embodiments, tivozanib is administered concurrent with the checkpoint inhibitor. In certain embodiments, tivozanib is administered subsequent to the checkpoint inhibitor. In certain embodiments, tivozanib and the checkpoint inhibitor are a first line therapy. In certain embodiments, the checkpoint inhibitor is a first line therapy and tivozanib is a second line therapy. In certain embodiments, the checkpoint inhibitor is a second line therapy and tivozanib is a third line therapy. In certain embodiments, the checkpoint inhibitor is a first line therapy and tivozanib is a third line therapy.

In certain embodiments of any of the foregoing methods, the method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle.

In certain embodiments of any of the foregoing methods, the subject is identified as having an International Metastatic-RCC Database Consortium (IMDC) risk score of favorable or intermediate prior to treating the subject. In certain embodiments, the IMDC risk category is favorable. In certain embodiments, the IMDC risk category is intermediate.

In certain embodiments of any of the foregoing methods, the subject was previously treated with at least two anti-cancer therapies (e.g., a first line anti-cancer therapy and a second line anti-cancer therapy). In one embodiment, the first line and second line anti-cancer therapies are both VEGFR TKI therapies. In another embodiment, the first and second line anti-cancer therapies are a VEGFR TKI and a checkpoint inhibitor, in either order, for example, the first line anti-cancer therapy is a VEGFR TKI and the second line therapy is a checkpoint inhibitor. In another embodiment, the first line and second line anti-cancer therapies are a VEGFR TKI and a systemic anti-cancer agent, in either order. In another embodiment, the first line and second line anti-cancer therapies are a checkpoint inhibitor and a systemic anti-cancer agent, in either order.

In another aspect, the invention provides a method of treating a subject suffering from refractory cancer wherein the subject has previously been treated with a vascular endothelial growth factor receptor tyrosine kinase inhibitor (VEGFR TKI) and a checkpoint inhibitor. The method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle. In one embodiment, the refractory cancer is refractory renal cell carcinoma.

In another aspect, the invention provides a method of treating a subject suffering from refractory cancer wherein the subject has been previously treated with two vascular endothelial growth factor receptor tyrosine kinase inhibitors (VEGFR TKI). The method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle. In one embodiment, the refractory cancer is refractory renal cell carcinoma.

In another aspect embodiment, the invention provides a method of treating a subject suffering from refractory cancer wherein the subject is identified as having an International Metastatic-RCC Database Consortium (IMDC) risk score of favorable or intermediate prior to treating the subject. The method comprises administering to the subject a pharmaceutical composition comprising 1.5 mg tivozanib for 21 days followed by 7 days without administration of tivozanib, wherein administering the tivozanib for 21 days followed by 7 days without administration constitutes a treatment cycle.

In certain embodiments of any of the foregoing methods, the refractory cancer is refractory renal cell carcinoma. In certain embodiments, tivozanib is administered in the form of tivozanib hydrochloride monohydrate. In certain embodiments, the subject undergoes one or more treatment cycles with tivozanib.

In certain embodiments of any of the foregoing methods, the VEGFR TKI is sorafenib, sunitinib, pazopanib, crizotinib, vandetinib, axitinib, cabozantinib, regorafenib, axinitib, or nintedanib. In certain embodiments, the checkpoint inhibitor is an anti-PDL1 or anti-PD1 inhibitor (e.g., nivolumab, pembrolizumab, cemiplimab, spartalizumab, camrelizumab, sintilimab, tislelizumab, toripalimab, prolgolimab, cetrelimab, pidilizumab, BMS-936559, MDX-1105, atezolizumab, durvalumab, or avelumab) or an anti-CTLA-4 inhibitor (e.g., ipilimumab). In certain embodiments, the systemic anti-cancer agent is everolimus or temsirolimus.

In certain embodiments of any of the foregoing methods, the subject undergoes one, two, three, four, five, six, seven, eight, nine, ten, eleven, twelve, or more than twelve treatment cycles. In certain embodiments, the subject exhibits a complete or partial response to tivozanib after one treatment cycle, after two treatment cycles, or after three, four, five, six, seven, eight, nine, ten, eleven, or twelve treatment cycles. In certain embodiments, the subject is administered tivozanib for one, two, three, four, five, six, seven, eight, nine, ten, eleven, twelve, or more than twelve months.

In certain embodiments of any of the foregoing methods, the dose of tivozanib is reduced when a subject experiences a ≥Grade 3 drug-related adverse event, moderate hepatic impairment (Child-Pugh class B), or severe hepatic impairment (Child-Pugh class C). In certain embodiments, the dose may be reduced to 1.0 mg daily, 1.5 mg every other day, or 1.0 mg every other day.

These and other aspects and features of the invention are described in the following detailed description and claims.

BRIEF DESCRIPTION OF THE DRAWINGS

The invention can be more completely understood with reference to the following drawings.

FIG. 3 is a tabulation of Best Overall Response (BOR) and Objective Response Rate (ORR) for subjects receiving tivozanib, compared to BOR and ORR for subjects receiving sorafenib. Numbers in parentheses show the percentage of patients falling within each category.

FIG. 4 is a tabulation of unstratified Kaplan-Meier Analysis of IRR Progression Free Survival for subjects receiving tivozanib, compared to PFS for subjects receiving sorafenib. Numbers in parentheses show the percentage of patients falling within each category.

FIG. 5 is a tabulation of the Kaplan-Meier Analysis of IRR Progression Free Survival for a subset of subjects who received Prior Check Point Inhibitor treatment comparing PFS for subjects receiving tivozanib, to PFS for subjects receiving sorafenib. Numbers in parentheses show the percentage of patients falling within each category.

FIG. 6 is a tabulation of the Kaplan-Meier Analysis of IRR Progression Free Survival stratified by IMDC Risk Category and Prior Therapy (As Randomized) in the Intent to Treat Population. Numbers in parentheses show the percentage of patients falling within each category.

FIG. 7 is a tabulation of the Kaplan-Meier Analysis of Overall Survival (OS) of subjects receiving tivozanib compared to subjects receiving sorafenib. Numbers in parentheses show the percentage of patients falling within each category.

FIG. 8 is a tabulation of the Kaplan-Meier Analysis of Overall Survival (OS) for a subset of subjects who received Prior Check Point Inhibitor treatment comparing OS for subjects receiving tivozanib, to OS for subjects receiving sorafenib. Numbers in parentheses show the percentage of patients falling within each category.

FIG. 9 is a Forest plot of Hazard Ratio with 95% Confidence Interval for Progression Free Survival of various patient subgroups.

FIG. 10 is a tabulation of the subgroup analysis of Progression Free Survival (PFS) using Cox Model in the intent to treat (ITT) population.

FIG. 12 is a tabulation of the subgroup of analysis of Overall Survival (OS) using Cox Model in the intent to treat (ITT) population.

FIG. 13 is a tabulation of the Best Overall Response Rate based on prior therapies.

FIG. 14 is a tabulation of the Duration of Response in the ITT population of subjects exhibiting objective response.

DETAILED DESCRIPTION OF THE INVENTION

Figure 1:
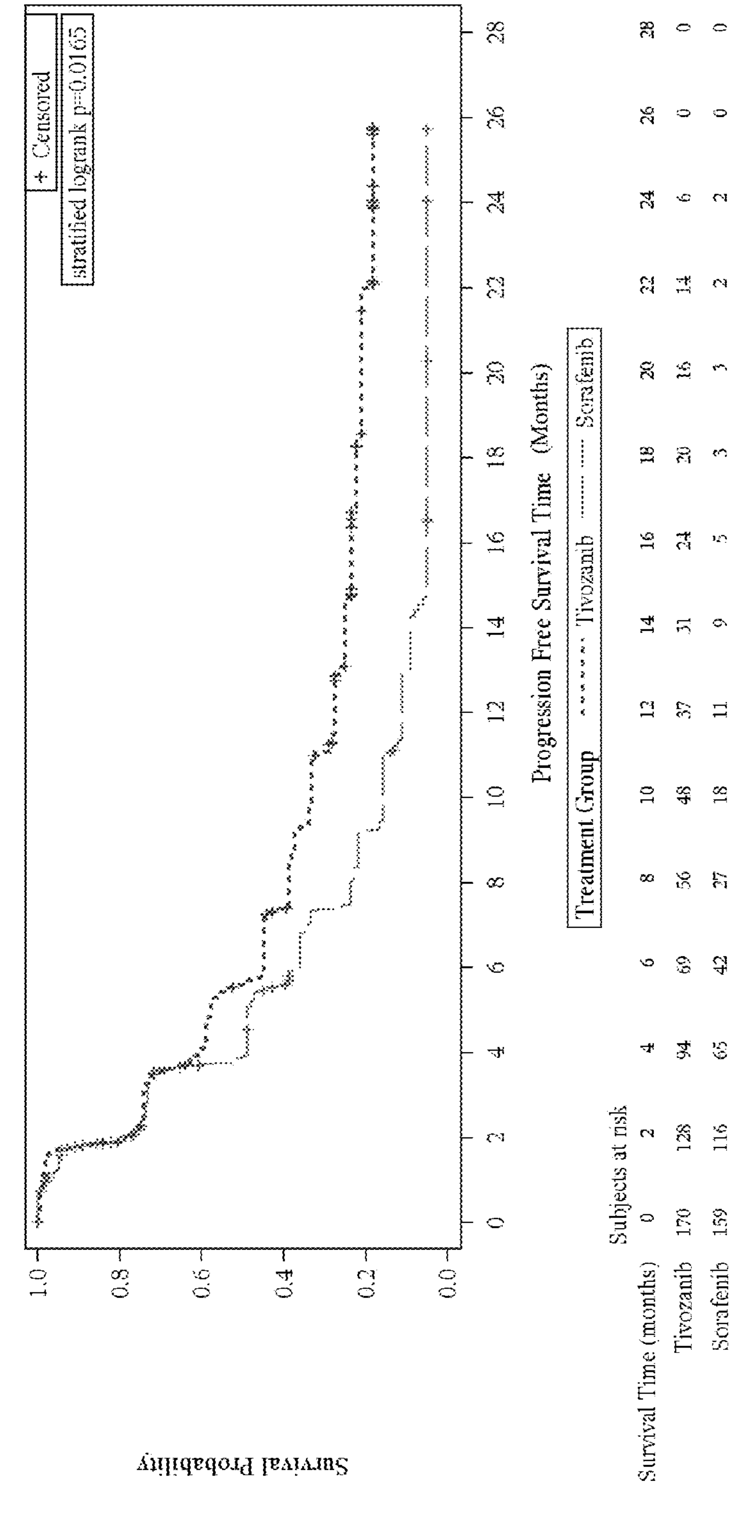
FIG. 1 illustrates the Kaplan-Meier Analysis of Independent Radiological Review (IRR) progression-free survival (PFS) in months stratified by IMDC (International Metastatic Renal Cell Carcinoma Database Consortium) risk and prior therapy for subjects receiving tivozanib, compared to PFS for subjects receiving sorafenib.

The invention generally relates to methods of treating cancer, for example, advanced or refractory cancer, with tivozanib. In one aspect, the invention relates to methods of (i) reducing tumor growth and/or (ii) increasing survival rates, such as progression free survival rates (PFS), of subjects suffering from an advanced or refractory cancer, e.g., renal cell carcinoma (RCC), e.g., advanced or refractory renal cell carcinoma. In certain embodiments, the disclosed methods are based on using tivozanib, a VEGF receptor tyrosine kinase inhibitor (VEGFR TKI), as a third line therapy in subjects suffering from RCC, e.g., advanced or refractory renal cell carcinoma, where first and second line treatments have failed to reduce tumor growth or increase survival rates, or where first and second line treatments have lost efficacy after initially successful treatment.

As shown in the examples that follow, tivozanib has a statistically significant effect on improving PFS in subjects suffering from RCC as compared to PFS in subjects treated with sorafenib, another VEGFR TKI. Without wishing to be bound by theory, it is believed that tivozanib's ability to suppress T-regulatory cells may explain, in part, tivozanib's superior performance as compared to sorafenib with respect to PFS and may also explain, in part, the relatively reduced occurrence and/or severity of adverse events (AEs) during treatment. For example, tivozanib demonstrated superior properties relative to sorafenib when used to treat subjects that had been previously subjected to treatment with a checkpoint inhibitor, such as a PD-1 or PD-L1 checkpoint inhibitor or a VEGFR TKI.

I. Definitions

For convenience, certain terms in the specification, examples, and appended claims are collected in this section.

As used herein, "pharmaceutically acceptable" or "pharmacologically acceptable" mean molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein, "tivozanib" means N-{2-chloro-4-[(6,7-dimethoxy-4-quinolyl)oxy]-phenyl}-N'-(5-methyl-3-isoxazolyl)urea and having the following chemical structure:

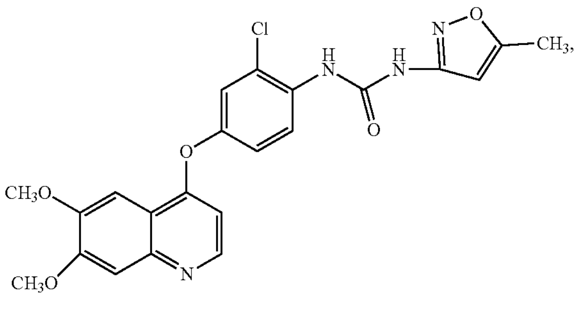

including pharmaceutically acceptable salts, solvates, solvates of a pharmaceutically acceptable salt, esters, or polymorphs thereof. See, for example, U.S. Pat. Nos. 6,821,987, 7,166,722 and 7,211,587, each of which are incorporated herein by reference in their entirety. In certain embodiments, tivozanib is N-{2-chloro-4-[(6,7-dimethoxy-4-quinolyl)oxy]-phenyl}-N'-(5-methyl-3-isoxazolyl)urea or hydrates of a hydrochloride salt. In certain embodiments, tivozanib is N-{2-chloro-4-[(6,7-dimethoxy-4-quinolyl)oxy]-phenyl}-N'-(5-methyl-3-isoxazolyl)urea monohydrochloric acid salt monohydrate. In certain embodiments, tivozanib is tivozanib hydrochloride having the chemical name 1-{2-chloro-4-[(6,7-dimethoxyquinolin-4-yl)oxy]phenyl}-3-(5-methylisoxazol-3-yl)urea hydrochloride hydrate having the chemical structure

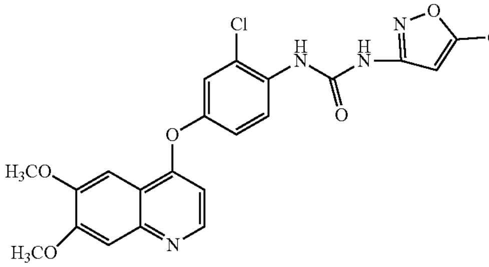

$\cdot HCl\cdot H_2O$, the molecular formula $C_{22}H_{19}ClN_4O_5\cdot HCl\cdot H_2O$, and a molecular weight of 509.34.

As used herein, the term "Progression-Free Survival (PFS)" is defined as the time from randomization to first documentation of objective tumor progression (progressive disease "PD", radiological) according to RECIST (Version 1.1; see, e.g., Eisenhauer et al. (2009), Eur. J. Cancer, 25:228-247) or death due to any reason, whichever comes first. PFS data is censored on the day following the date of last tumor assessment documenting absence of PD for subjects who do not have objective tumor progression and are still on study at the time of the analysis, are given anti-tumor treatment other than the study treatment, or are moved from treatment follow-up prior to documentation of objective tumor progression. Subjects having no tumor assessments after randomization who are not known to have died have PFS censored on the date of randomization.

As used herein, the term "Overall survival (OS)" is defined as the time from the date of randomization to date of death due to any cause. In the absence of confirmation of death, survival time is censored at the last date the subject is known to be alive. Subjects lacking data beyond randomization have their survival times censored on the date of randomization.

As used herein, the term "Objective response rate (ORR)" is defined as the proportion of subjects with confirmed complete response (CR) or confirmed partial response (PR) according to RECIST (Version 1.1), relative to the total population of randomized subjects. Confirmed responses are those that persist on repeat imaging study at least 4 weeks after the initial documentation of response.

As used herein, the term "Duration of response (DoR)" is defined as the time from the first documentation of objective tumor response to the first documentation of objective tumor progression or to death due to any cause. DoR data is censored on the day following the date of the last tumor assessment documenting absence of PD for subjects who do not have tumor progression and are still on the study at the time of an analysis, are given antitumor treatment other than the study treatment, are removed from the study follow-up prior to documentation of objective tumor progression, died of non-cancer related cause, including death due to unknown cause in the absence of documented disease progression. DoR is only calculated for the subgroup of subjects with an objective tumor response (PR or CR).

As used herein, the terms "response" or "responding" in the context of a subject's response to tivozanib refer to the RECIST (Response Evaluation Criteria in Solid Tumors, version 1.1, 2009) criteria for evaluating response of target lesions to a cancer therapy. According to the RECIST criteria, subjects who respond are categorized as either "complete responders" (disappearance of all target lesions) or "partial responders" (at least a 30% decrease in the sum of the longest diameter of target lesions, taking a reference the baseline sum longest diameter); non-responders are placed into one of two categories: stable disease (neither sufficient shrinkage to qualify for partial response nor sufficient increase to qualify for progressive disease, taking as reference the smallest sum longest diameter since start of treatment) or progressive disease (at least a 20% increase in the sum of the longest diameter of target lesions, taking as reference the smallest sum longest diameter recorded since treatment started or the appearance of one or more new lesions). The RECIST criteria are discussed in detail in, e.g., Therasse et al., J. Natl. Cancer Inst., 2000: 92:205-216 (RECIST 1.0), and Eisenhauer et al., Eur. J. Cancer, 2009: 25:228-247 (RECIST 1.1). Accordingly, as described herein, responding to therapy refers to subjects falling within the RECIST categories of complete or partial responder, whereas not responding refers to subjects falling within the RECIST categories of stable disease or progressive disease.

As used herein, the terms "treating" or "treat" or "treatment" in the context of cancer refer to applying techniques, actions or therapies to a subject that (a) slow tumor growth, (b) halt tumor growth, (c) promote tumor regression or disappearance, (d) ameliorate a symptom of the cancer, (e) cure the cancer, or (f) prolong survival of the subject, or applying techniques, actions or therapies to a subject in an attempt to achieve any of (a)-(f) regardless of whether the individual actually responds to the technique, action or therapy.

As used herein, the term "clinical benefit" refers to a subject experiencing any of (a) slowing of tumor growth, (b) halting of tumor growth, (c) tumor regression or disappearance, (d) amelioration of a symptom of the cancer, (e) curing the cancer, or (f) prolonging survival of the subject.

As used herein, "advanced" with respect to a cancer or tumor (e.g., renal cell carcinoma) refers to cancer or tumor that has reached Stage 3 or Stage 4. In certain embodiments, “advanced” means that the cancer or tumor has metastasized, or otherwise cannot be adequately treated with local therapy, such as surgical intervention or radiation therapy, alone, and therefore requires a systemic therapy. In certain embodiments, “advanced” means that the cancer or tumor has recurred after having responded to treatment with a local or systemic therapy.

As used herein, “refractory” refers to a cancer or tumor in a subject that fails to respond to a mode of treatment, e.g., the subject fails to attain a clinical benefit, or experiences disease progression. A particular type of cancer or tumor may be refractory to an initial treatment, or may initially respond, but may at a later time fail to further respond, develop resistance or otherwise become “refractory” to such treatment. In certain embodiments, “refractory” refers to a cancer or tumor, such as a renal cell carcinoma, that has been treated with at least one systemic treatment, and has not responded to such treatment, or has continued to progress after such treatment. In another embodiment, “refractory” refers to a cancer or tumor, such as renal cell carcinoma, that has been treated with at least two systemic treatments, and has not responded to such treatments, or has continued to progress after such treatments.

As used herein, the terms “subject” and “patient” are used interchangeably and refer to an organism to be treated by the methods and compositions of the present invention. Such organisms are preferably a mammal (e.g., human, mouse, rat, guinea pig, dog, cat, horse, cow, pig, or non-human primate, such as a monkey, chimpanzee, baboon, and rhesus), and more preferably, a human.

As used herein, the term “drug related adverse event,” “adverse event” or “AE” refers to adverse events as defined and classified in the National Cancer Institute—Common Terminology Criteria for Adverse Events (CTCAE) version 4.03 dated Jun. 14, 2010, and any reference to “Grade” of adverse event refers to the grading system as outlined therein.

As used herein, the term “pharmaceutical composition” refers to the combination of an active agent with a carrier, inert or active, making the composition especially suitable for diagnostic or therapeutic use in vivo or ex vivo.

As used herein, the term “International Metastatic-RCC Database Consortium (IMDC) risk score refers to a risk score for RCC determined based upon the following criteria:

| IMDC CLASSIFICATION CRITERION | NO | YES |
|---|---|---|
| <1 year from time of diagnosis to systemic therapy | 0 | +1 |
| Kamofsky Performance Status <80% | 0 | +1 |
| Hemoglobin < lower limit of normal [Usually ~120 g/L or 12 g/dL] | 0 | +1 |
| Corrected calcium > upper limit of normal [Usually ~8.5-10.2 mg/dL] | 0 | +1 |
| Neutrophils > upper limit of normal [Usually ~2.0-7.0 × $10^9$/L] | 0 | +1 |
| Platelets > upper limit of normal [Usually ~150,000-400,000 cells/μL] | 0 | +1 |

For example, a “favorable” IMDC score is 0, whereas an “intermediate” score is 1-2, and a “poor” score is 3 based on these criteria, as shown below.

| RISK CATEGORY | IMDC No. | MEDIAN SURVIVAL* |
|---|---|---|
| Favorable | 0 | 35.3-43.2 mos |
| Intermediate | 1-2 | 16.6-22.5 mos |
| Poor | 3+ | 5.4-7.8 mos |

*Median Survival ranges based on the following references: https://www.mdcalc.com/imdc-international-metastatic-rcc-database-consortium-risk-score-rcc Ko et al. (2015) The Lancet 16: 293-300.

As used herein, the term “effective amount” refers to the amount of an active agent (e.g., tivozanib) sufficient to effect beneficial or desired results, such as, for example, to effect a clinical benefit in a subject. An effective amount can be administered in one or more administrations, applications or dosages and is not intended to be limited to a particular formulation or administration route.

As used herein, the term “effective treatment regimen of tivozanib” refers to a treatment regimen of tivozanib sufficient to effect beneficial or desired results, such as to effect a clinical benefit in a subject. An effective treatment regimen of tivozanib can be administered in one or more administrations, applications or dosages and is not intended to be limited to a particular formulation or administration route. An exemplary effective treatment regimen of tivozanib is a regimen that is effective to elicit a complete or partial response according to RECIST (Version 1.1) criteria, as further defined herein. An exemplary effective treatment regimen of tivozanib is administration of at least one treatment cycle with tivozanib, where a treatment cycle comprises administering 1.5 mg tivozanib for 21 days followed by 7 days without administration of tivozanib.

The methods and compositions described herein can be used alone or in combination with other therapeutic agents and/or modalities. The term administered “in combination,” as used herein, is understood to mean that two (or more) different treatments are delivered to the subject during the course of the subject’s affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as “simultaneous” or “concurrent delivery.” In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

II. Methods of Treatment

The invention involves methods of treating cancers, for example, difficult-to-treat cancers, such as renal cell carcinoma, with tivozanib. In one embodiment, tivozanib is used to treat renal cell carcinoma where traditional first and second line therapies have failed to treat the cancer. In particular, the method of the invention is suitable for treating renal cell carcinoma in a subject as a third line therapy. In one embodiment, the renal cell carcinoma is refractory advanced renal cell carcinoma. In another embodiment, the renal cell carcinoma is metastatic. That is, the cancer cells have begun to migrate to other sites in the body, primarily through the blood and/or lymphatic systems, and form new tumors which retain characteristics of the original or primary tumors.

In modern clinical practice, it is becoming more common for subjects to be treated by multiple anti-cancer therapies, both in combinations and sequentially. In one embodiment, the invention provides methods of treating refractory cancer in a subject who has been previously treated with at least one prior therapy (e.g., a first line treatment). In one embodiment, tivozanib may be administered subsequent to such first line treatment (e.g., as second-line treatment). In another embodiment, tivozanib may be administered in combination with the first line treatment, so that the refractory cancer may further respond to the first line treatment and/or respond to treatment with tivozanib. In another embodiment, tivozanib may be administered in combination with or prior to another treatment different from the first line treatment (e.g., second line treatment). The first and second line treatments may be selected from a wide range of anti-cancer agents, including but not limited to tyrosine kinase inhibitors (TKIs); VEGFR inhibitors (including anti-VEGFR antibodies and VEGFR TKIs); checkpoint inhibitors, and other systemic anti-cancer agents. In one embodiment, tivozanib may be administered subsequent to such first and second-line treatments (e.g., as a third-line treatment). In another embodiment, tivozanib may be administered in combination with one or both of the first and second line treatments, so that the refractory cancer may further respond to one or more of the first and second line treatments and/or respond to treatment with tivozanib. In other embodiments, tivozanib may be administered in combination with, or subsequent to additional lines of treatment (e.g., as a fourth-line treatment, a fifth-line treatment, etc.).

In one embodiment, the invention provides methods of treating refractory cancer, such as advanced renal cell carcinoma, with tivozanib in a subject previously treated with at least one therapy (e.g., a first line treatment). In one embodiment, the first line treatment is a TKI or a VEGFR TKI. In another embodiment, the first line treatment is a checkpoint inhibitor. In another embodiment, the first line treatment is a systemic anti-cancer agent other than a TKI or a checkpoint inhibitor.

In one embodiment, the invention provides methods of treating refractory advanced renal cell carcinoma with tivozanib in a subject previously treated with at least two therapies (e.g., a first line treatment and a second line treatment). In one embodiment, the subject was previously treated with at least two different tyrosine kinase inhibitors (TKIs) or in particular, two or more vascular endothelial growth factor receptor tyrosine kinase inhibitors (VEGFR TKI). In another embodiment, the subject was previously treated with at least one TKI or VEGFR TKI and at least one checkpoint inhibitor. In another embodiment, the subject was previously treated with at least one TKI or at least one VEGFR TKI and at least one other systemic anti-cancer agent. In another embodiment, the subject was previously treated with at least one checkpoint inhibitor and at least one other systemic anti-cancer agent. In another embodiment, the subject was previously treated with at least two TKIs or VEGFR TKIs, and at least one checkpoint inhibitor.

In one embodiment, the invention provides methods of treating refractory advanced renal cell carcinoma in a subject identified as having a favorable or intermediate International Metastatic-RCC Database Consortium (IMDC) risk score by administering tivozanib. For example, in one embodiment, the subject has a favorable risk score of 0. In another embodiment, the subject has an intermediate risk score of 1 or 2.

Refractory cancers according to the present invention can broadly be any type of cancer, including, but not limited to, lung cancer, liver cancer, ovarian cancer, prostate cancer, testicular cancer, gallbladder cancer, sarcoma, Ewing sarcoma, thyroid cancer, melanoma, skin cancer, pancreatic cancer; gastrointestinal/stomach (GIST) cancer, lymphoma, head and neck cancer, glioma or brain cancer, colon cancer, rectal cancer, breast cancer, renal cell carcinoma or kidney cancer. In one embodiment, the refractory cancer is renal cell carcinoma.

A non-exhaustive list of TKIs with which a subject according to the invention may be treated, or may have been previously treated, include imatinib, gefitinib, erlotinib, sorafenib, dasatinib, sunitinib, lapatinib, nilotinib, pazopanib, crizotinib, alunbrig, ruxolitinib, vandetinib, vemurafenib, axitinib, bosutinib, cabozantinib, regorafenib, vismodegib, ponatinib, ibrutinib, acalabrutinib, alectinib, axinitib, or nintedanib.

A non-exhaustive list of VEGFR TKIs with which a subject according to the invention may be treated, or may have been previously treated, include sunitinib, pazopanib, crizotinib, vandetinib, axitinib, cabozantinib, regorafenib, axinitib, or nintedanib. For purposes of the present invention, anti-VEGFR antibodies, such as bevacizumab, may be used in any instance where a VEGFR TKI inhibitor may be used, and thus may substitute for a VEGF TKI in any of the methods of the present invention.

A non-exhaustive list of checkpoint inhibitors with which a subject according to the invention may be treated, or may have been previously treated include the anti-PD1 antibodies nivolumab, pembrolizumab, cemiplimab, spartalizumab, camrelizumab, sintilimab, tislelizumab, toripalimab, prolgolimab cetrelimab, and pidilizumab; the anti-PDL1 antibodies atezolizumab, durvalumab, avelumab or BMS-936559 (MDX-1105); and the anti-CTLA4 antibody ipilimumab.

A non-exhaustive list of other systemic anti-cancer agents with which subjects according to the invention may be treated, or may have been previously treated include mTOR inhibitors, such as sirolimus, everolimus and temsirolimus; topoisomerase inhibitors, such as irinotecan and topotecan; platinum-based therapeutics, also referred to as platins, such as cisplatin, carboplatin, oxaliplatin and nedaplatin; taxanes, such as paclitaxel, docetaxel and cabazitaxel; poly ADP ribose polymerase (PARP) inhibitors, such as olaparib, rucaparib and niraparib; anti-apoptotic protein inhibitors, such as venetoclax and blinatumomab; phosphatidylinositol 3 kinase (PI3K) inhibitors, such as idelalisib, copanlisib, buparlisib and duvelisib; proteasome inhibitors such as bortezomib, carfilzomib and ixazomib; HDAC inhibitors such as vorinostat, romidepsin, panobinostat and belinostat; CDK inhibitors such as palbociclib, ribociclib and abemaciclib; growth factor antagonists, such as olaratumab, cetuximab, necitumumab, panitumumab and osimertinib; anti-tumor antigen antibodies, such as rituximab, ofatumumab, obinutuzumab, ibritumomab, daratumumab, dinutuximab, trastuzumab, ado-trastuzumab emtansine, pertuzumab, and brentuximab vedotin; aromatase inhibitors such as exemestane, anastazole and letrozole; hedgehog pathway inhibitors, such as sonidegib and vismodegib; folic acid inhibitors, such as pemetrexed; or nucleoside or microtubule inhibitors that interfere with normal DNA synthesis, protein synthesis, cell replication, or otherwise inhibit rapidly proliferating cells. Such nucleoside and microtubule inhibitors include trabectedin, mechlorethamine, vincristine, temozolomide, cytarabine, lomustine, azacitidine, omacetaxine mepesuccinate, asparaginase, eribulin mesylate, cabazitaxel, capacetrine, bendamustine, ixabepilone, nelarabine, clorafabine, and trifluridine/tipiracil.

In one embodiment, subjects treated with tivozanib according to the methods of the invention (e.g., as a second or third line treatment) have an objective response rate (ORR) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the baseline ORR of subjects receiving sorafenib (e.g., as a second or third line treatment) or subjects receiving no treatment (e.g., no second or third line treatment).

In one embodiment, subjects treated with tivozanib according to the methods of the invention (e.g., as a second or third line treatment) have an objective response rate (ORR) that is at least 1.25 times, at least 1.50 times greater, at least 1.75 times, at least 2 times, at least 2.25 times, or at least 2.50 times great than the baseline ORR of subjects receiving sorafenib (e.g., as a second or third line treatment) or subjects receiving no treatment (e.g., no second or third line treatment). In one embodiment, subjects treated with tivozanib according to the methods of the invention (e.g., as a second or third line treatment) have an ORR that is at least 2.25 times greater than the baseline ORR of subjects receiving sorafenib (e.g., as a second or third line treatment).

In one embodiment, subjects treated with tivozanib according to the methods of the invention (e.g., as a second or third line treatment) have a rate of progression-free survival (PFS) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the baseline rate of PFS of subjects receiving sorafenib (e.g., as a second or third line treatment) or subjects receiving no treatment (e.g., no second or third line treatment).

In one embodiment, subjects treated with tivozanib according to the methods of the invention (e.g., as a second or third line treatment) have a median progression-free survival (PFS) that is at least 1.25 times, at least 1.50 times, at least 1.75 times, at least 2 times, at least 2.25 times, or at least 2.50 times greater than the median PFS of subjects receiving sorafenib (e.g., as a second or third line treatment) or subjects receiving no treatment (e.g., no second or third line treatment). In one embodiment, subjects treated with tivozanib according to the methods of the invention (e.g., as a second or third line treatment) have a median PFS that is at least 2.25 times greater than the median PFS of subjects receiving sorafenib (e.g., as a second or third line treatment).

In one embodiment, subjects treated with tivozanib according to the methods of the invention (e.g., as a second or third line treatment) have a median progression-free survival (PFS) of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months longer than the median PFS for subjects receiving sorafenib (e.g., as a second or third line treatment), or than subjects receiving no treatment (e.g., no second or third line treatment). In one embodiment, the median progression-free survival (PFS) is at least 5 months.

In one embodiment, subjects treated with tivozanib and previously treated with at least one checkpoint inhibitor according to the methods of the invention have a median progression-free survival (PFS) of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months longer than the median PFS for subjects receiving sorafenib, or than subjects receiving no treatment. In one embodiment, the median progression-free survival (PFS) is at least 7 months.

In one embodiment, subjects treated with tivozanib and previously treated with one VEGFR TKI and one checkpoint inhibitor according to the methods of the invention have a median progression-free survival (PFS) of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months longer than the median PFS for subjects receiving sorafenib as a third line treatment, or than subjects receiving no third line treatment. In one embodiment, the median progression-free survival (PFS) is at least 7 months.

In one embodiment, subjects treated with tivozanib according to the methods of the invention (e.g., as a second or third line treatment) have an overall survival (OS) rate that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the baseline OS rate of subjects receiving sorafenib (e.g., as a second or third line treatment) or subjects receiving no treatment (e.g., no second or third line treatment).

In one embodiment, subjects treated with tivozanib according to the methods of the invention (e.g., as a second or third line treatment) have a median overall survival (OS) rate of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months longer than the baseline median OS of subjects receiving sorafenib (e.g., as a second or third line treatment), or than subjects receiving no treatment (e.g., no second or third line treatment).

In one embodiment, subjects treated with tivozanib according to the methods of the invention (e.g., as a second or third line treatment) have a duration of response (DoR) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the baseline DoR of subjects receiving sorafenib (e.g., as a second or third line treatment) or subjects receiving no treatment (e.g., no second or third line treatment).

In one embodiment, subjects treated with tivozanib according to the methods of the invention (e.g., as a second or third line treatment) have a duration of response (DoR) that is at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months longer than the baseline DoR of subjects receiving sorafenib (e.g., as a second or third line treatment), or than subjects receiving no treatment (e.g., no second or third line treatment). In one embodiment, for subjects treated with tivozanib according to the methods of the invention, the $25^{th}$ percentile of the duration of response (DoR) is at least 9 months.

In one embodiment, subjects treated with tivozanib according to the methods of the invention have a median progression-free survival (PFS) of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months. In one embodiment, the median progression-free survival (PFS) is at least 5 months.

In one embodiment, subjects treated with tivozanib and previously treated with at least one checkpoint inhibitor according to the methods of the invention have a median progression-free survival (PFS) of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months. In one embodiment, the median progression-free survival (PFS) is at least 7 months.

In one embodiment, subjects treated with tivozanib and previously treated with one VEGFR TKI and one checkpoint inhibitor according to the methods of the invention have a median progression-free survival (PFS) of at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months. In one embodiment, the median progression-free survival (PFS) is at least 7 months.

In one embodiment, subjects treated with tivozanib according to the methods of the invention have a duration of response (DoR) that is at least one month, at least two months, at least three months, at least four months, at least 5 months, at least 6 months, at least 7 months, at least eight months, at least nine months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, at least 36 months, at least 37 months, at least 38 months, at least 39 months, at least 40 months, at least 41 months, at least 42 months, at least 43 months, at least 44 months, at least 45 months, at least 46 months, at least 47 months, at least 48 months, at least 49 months, at least 50 months, at least 51 months, at least 52 months, at least 53 months, at least 54 months, at least 55 months, at least 56 months, at least 57 months, at least 58 months, at least 59 months, or at least 60 months.

According to certain embodiments of the invention, treatment with tivozanib is indicated as long as a clinical benefit is observed in the subject or until unacceptable toxicity occurs.

III. Dosage

Exemplary effective amounts, dosages, or treatment regimens of tivozanib include 0.5-3 mg, 0.5-2 mg, 1-3 mg, 0.5-1.5 mg, 1.0-2.0 mg, 1.0-1.5 mg. 1.4-1.6 mg, 0.8-0.9 mg, 0.9-1.0 mg, 0.9-1.1 mg, 1.0-1.1 mg, 1.1-1.2 mg, 1.2-1.3 mg, 1.3-1.4 mg, 1.4-1.5 mg, 1.4-1.6 mg, 1.5-1.6 mg, 1.6-1.7 mg, 1.7-1.8 mg, 1.8-1.9 mg, 1.8-2.0 mg or 1.9-2.0 mg daily or every other day.

The amount administered will depend on variables such as the type and extent of disease or indication to be treated, the overall health of the patient, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study. Dosing frequency can vary, depending on factors such as route of administration, dosage amount, and the disease being treated. Exemplary dosing frequencies are once per day, once every other day, once every three days, once every four days, once every five days, once every six days, once per week and once every two weeks.

In one embodiment, the dosage of tivozanib is 1.5 mg daily. In another embodiment, the dosage is 1.0 mg daily. Additional exemplary effective amounts, dosages, or treatment regimens of tivozanib are described in U.S. Pat. Nos. 6,821,987, and 7,166,722.

According to one embodiment, the dosage is 1.0 mg daily of tivozanib hydrochloride (equivalent to 0.89 mg tivozanib free base). According to another embodiment, the dosage is 1.5 mg daily of tivozanib hydrochloride (equivalent to 1.34 mg tivozanib free base). In one embodiment, the dose is 1.34 mg daily of tivozanib free base. In another embodiment, the dose is 0.89 mg daily of tivozanib free base.

According to one embodiment, a 1.5 mg daily dose of tivozanib is reduced to 1.0 mg daily when a subject experiences a ≥Grade 3 drug-related adverse event.

According to one embodiment, a 1.5 mg daily dose of tivozanib is reduced to 1.5 mg every other day for a subject experiencing moderate hepatic impairment (Child-Pugh class B).

According to one embodiment, a 1.5 mg daily dose of tivozanib is reduced to 1.0 mg every other day for a subject experiencing severe hepatic impairment (Child-Pugh class C).

In one embodiment, the dose is 1.5 mg daily of tivozanib hydrochloride administered for 21 days followed by 7 days without administration.

IV. Administration Protocol

Tivozanib may be administered as an oral tablet or capsule or as an intravenous (IV) infusion. When administered as an oral tablet or capsule, the dosage of tivozanib may be provided in a single capsule or tablet or in two or more capsules or tablets.

Exemplary effective amounts, dosages, or treatment regimens of tivozanib include administration on a repeating schedule of one dose (e.g., a single dosage contains 0.5-2.0 mg of tivozanib) per day for three weeks, followed by one week off (i.e., 3 weeks on, 1 week off). For example, tivozanib may be administered on a repeating schedule of 0.5-3 mg, 0.5-2 mg, 0.5-1.5 mg, 1.0-3.0 mg, 1.0-2.0 mg, 1.0-1.5 mg, or 1.4-1.6 mg per day for three weeks, followed by one week off (i.e., 3 weeks on, 1 week off). The period of time beginning from Day 1 of administration to the last day of the week off may be referred to as a treatment cycle. In other embodiments, tivozanib may be administered as one dose (e.g., a single dosage contains 0.5-2.0 mg of tivozanib) per day. For example, tivozanib may be administered at a dose of 0.5-3 mg, 0.5-2 mg, 0.5-1.5 mg, 1.0-3.0 mg, 1.0-2.0 mg, 1.0-1.5 mg or 1.4-1.6 mg, 1 mg, or 1.5 mg daily.

In one embodiment, tivozanib is administered in an amount of 1.5 mg per day. In another embodiment, tivozanib is administered in an amount of 1.0 mg per day. In another embodiment, tivozanib is administered in an amount of 1.5 mg per day every day for three weeks (i.e., 21 days), followed by one week (i.e., 7 days) with no dose of tivozanib (i.e., 3 weeks on, 1 week off), where three weeks on tivozanib and one week off constitutes a 4 week treatment cycle.

In one embodiment, tivozanib is orally administered in an amount of 1.5 mg daily for three weeks, followed by one week off, while in another embodiment, tivozanib is administered in an amount of 1.0 mg daily for three weeks, followed by one week without administration of tivozanib. According to these embodiments, three weeks on and one week off constitutes a 4 week treatment cycle.

In one embodiment, tivozanib is orally administered in an amount of 1.5 mg daily and reduced to 1.0 mg daily when the subject experiences a ≥Grade 3 drug-related adverse event. In this embodiment, the administration period for tivozanib is three weeks (starting from the first 1.5 mg dose), followed by one week without administration of tivozanib. According to this embodiment, three weeks on and one week off constitutes a 4-week treatment cycle.

In one embodiment, tivozanib is orally administered in an amount of 1.5 mg daily and is reduced to 1.5 mg every other day when the subject develops moderate hepatic impairment (Child-Pugh Class B). In this embodiment, the administration period is 3 weeks (starting from the first 1.5 mg dose) followed by one week without administration. According to this embodiment, three weeks on and one week off constitutes a 4-week treatment cycle.

In one embodiment, tivozanib is orally administered in an amount of 1.5 mg daily and is reduced to 1.0 mg every other day when a subject develops severe hepatic impairment (Child-Pugh Class C). In this embodiment, the administration period is 3 weeks followed by one week without administration. According to this embodiment, three weeks on and one week off constitutes a 4-week treatment cycle.

According to one embodiment, a subject undergoes one, two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, or 36 treatment cycles of tivozanib, for example, four-week treatment cycles of tivozanib, for example, where the treatment cycle is three weeks on, one week off According to one embodiment, a treatment cycle (for example, a four-week treatment cycle) is repeated as long as the subject experiences a clinical benefit or until the subject experiences unacceptable toxicity.

In a further embodiment, tivozanib is administered as a capsule. In a further embodiment, the capsule contains gelatin. In yet another embodiment, the capsule contains gelatin and titanium dioxide.

In a further embodiment, tivozanib is formulated as a pharmaceutical composition with mannitol and magnesium stearate. In other embodiments, other pharmaceutically acceptable carriers may be used.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a 10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The invention is further illustrated by the following examples. The following examples are provided for illustration purposes only, and are not to be construed as limiting the scope or content of the invention in any way.

1. Phase 3 Clinical Trial Demonstrates Tivozanib's Beneficial Effects in Treating Refractory Advanced RCC a. Study Design A randomized, controlled, open-label, multi-center Phase 3 study comparing treatment with tivozanib to treatment with sorafenib with refractory advanced renal cell carcinoma (RCC) was undertaken. Sorafenib was chosen as the comparator for this Phase 3 trial because it is a VEGFR inhibitor that is approved for treatment of advanced RCC, and has been previously evaluated in prior clinical studies in the refractory setting.

Subjects were randomized (1:1) to treatment with tivozanib or sorafenib. The randomization of subjects was stratified according to the International Metastatic Renal Cell Carcinoma Database Consortium (IMDC) risk category (favorable, intermediate, poor) and according to prior therapy which could be: 1) two prior VEGFR TKIs; 2) a check point inhibitor (e.g., a PD-1 or PDL-1 inhibitor) and a prior VEGFR TKI; or 3) a VEGFR TKI plus any other systemic agent. Once the strata were identified, treatment was randomly assigned to a subject with the strata using a complete permuted block design in an unblended fashion (open-label). In the event a subject had previously received treatment with two VEGFR TKIs and a checkpoint inhibitor, the patient was stratified according to the most recent line of therapy.

The maximum tolerated dose (MTD) of tivozanib was determined to be 1.5 mg/day based on data from a previous study KRN951/03-BO1, where 3 of 8 subjects in the 2 mg/day tivozanib group experienced a dose limiting toxicity (DLT), indicating that the maximum tolerated dose had been exceeded. The safety of the MTD of 1.5 mg/day was confirmed in multiple subsequent studies. In that same study, it was determined that toxicities were rapidly reversible upon stopping treatment with tivozanib.

The dosing regimen for the Phase 3 trial was 1.5 mg/day given continuously for 21 days followed by a 7-day break, i.e., 3 weeks on, 1 week off. This dose was shown to be well tolerated in study subjects enrolled in a previous study AV-951-07-201, where only 8.5% (23/272) study subjects required a dose reduction and only 2.9% (8/272) required a dose interruption. The 7-day break was utilized in an effort to maximize clinical benefit while giving study subject an opportunity to recover from any toxicities.

b. Study Objectives and Purpose

The primary objective of the Phase 3 Trial was to compare the progression-free survival (PFS) of subjects with refractory advanced RCC randomized to treatment with tivozanib or sorafenib as assessed by blinded independent radiological review (IRR) of computerized tomography (CT) and/or magnetic resonance imaging (MRI).

The secondary objectives of this study were (1) to compare the overall survival (OS) of subjects randomized to treatment with tivozanib or sorafenib; (2) to compare objective response rate (ORR) and duration of response (DoR) of subjects randomized to treatment with tivozanib or sorafenib; and (3) to compare the safety and tolerability of tivozanib and sorafenib.

Tertiary objectives of this study were to explore any relationship between tivozanib and sorafenib drug levels and activity and tivozanib and sorafenib drug levels and adverse events (AEs).

c. Subject Inclusion Criteria and Enrollment

Subjects were enrolled beginning approximately June 2016 through August 2017. A total of approximately 350 subjects were enrolled, of which approximately 343 were randomized for treatment with either tivozanib or sorafenib. The study was open to males and females meeting the following eligibility criteria:

1. At least 18 years of age.
2. Subjects with metastatic RCC who have failed 2 or 3 prior systemic regimens, one of which includes a VEGFR TKI other than sorafenib or tivozanib.
   a. Postoperative or adjuvant systemic therapy was not counted as a prior therapy unless recurrence was detected within 6 months of completion of treatment, in which case it was counted as a prior therapy for metastatic disease.
   b. Subjects had to be off all systemic anti-cancer therapy or radiotherapy for at least 2 weeks prior to Cycle 1 Day 1.
3. Subjects must have recovered from the adverse events (AEs) of prior therapy or returned to baseline. Controlled AEs such as hypothyroidism or hypertension were permitted.
4. Histologically or cytologically confirmed RCC with a clear cell component (subjects with pure papillary cell tumor or other non-clear cell histologies, including collecting duct, medullary, chromophobe, and unclassified RCC were excluded).
5. Measurable disease per the RECIST criteria (Version 1.1).
6. ECOG performance status of 0 or 1.
7. Life expectancy ≥3 months.

d. Tivozanib Administration

Tivozanib hydrochloride was administered orally, at a dose of 1.5 mg/day, beginning on Day 1 of Cycle 1. Subjects received tivozanib once daily for 3 weeks followed by 1 week off the study drug (1 cycle=3 weeks on, 1 week off). One cycle was defined as 4 weeks of treatment. Cycles were repeated every 4 weeks. Tivozanib was administered as a 1.5 mg capsule that was to be swallowed whole without crushing or opening.

The prescribed daily dose of tivozanib was taken, preferably in the morning, with water. Tivozanib was taken at least 1 hour before or 2 hours after ingesting any food or other medications. Grapefruit juice was contraindicated during the study. Treatment with tivozanib was continued if tolerated and in the absence of documented disease progression. If a dose was vomited or if a dose was missed for any reason, the dose was not made up. If Day 1 of a cycle was delayed for any reason, the complete 21 days of tivozanib were administered once the cycle started. Only one tivozanib capsule (1.5 mg) was taken each day.

Dose reductions of tivozanib to 1.0 mg/day were allowed for subjects with ≥Grade 3 drug-related adverse events. The exception was hypertension, which was treated with anti-hypertensive drugs prior to dose reduction. Once the dose of tivozanib was reduced, it could not be re-escalated throughout the study. If a subject was unable to tolerate a dose of 1.0 mg/day due to toxicities thought to be related to tivozanib, dosing with tivozanib was discontinued.

Subjects with Grade 4 drug-related toxicity, or Grade 3 drug-related toxicity that was persistent despite appropriate medical care, had their dose interrupted to allow for resolution of the toxicity. Tivozanib administration was permitted to be interrupted for up to 4 weeks. If a subject was able to resume treatment after interruption of ≤4 weeks, missed doses were not made up (i.e., cycle duration will remain unchanged). If any drug-related toxicity resulted in an interruption of >4 weeks, the subject was discontinued from the study unless there was a clear benefit from treatment.

e. Duration of Treatment

Subjects with documented stable disease or an objective response were permitted to receive therapy at the same dose and schedule until disease progression or unacceptable toxicities occurred, or if other withdrawal criteria were met.

Subjects experiencing unacceptable toxicities were discontinued from further study treatment. Subjects with radiological evidence of progressive disease (per RECIST Version 1.1) per investigator/local radiology assessment continued treatment until progressive disease was verified by an independent radiologist. Verification of progressive disease was not required when a patient demonstrated significant clinical deterioration that is compatible with progressive disease. Subjects with documented disease progression (as verified by an independent radiologist) were discontinued from the study treatment.

f. Analysis of Endpoints

Three populations were used in the analyses of the data:

1. The intent-to-treat (ITT) population which consisted of all randomized subjects; this population was used for efficacy analysis, including primary endpoint (progression-free survival). Subjects were analyzed as randomized.
2. The per protocol (PP) population which was defined as all randomized subjects who received at least two cycles (8 weeks) of protocol treatment (unless discontinued due to death or disease progression), had no major protocol deviations that confounded the effects of treatment, and met all eligibility criteria. Major protocol deviations included but were not limited to failure to satisfy eligibility criteria and taking prohibited medications during the treatment phase of the study. Subjects were analyzed as treated.
3. The safety population (SAF) which included all subjects who received at least one dose of either study drug. Subjects were analyzed as treated.

The primary efficacy endpoint (PFS) and secondary efficacy endpoints (OS, ORR, and DoR) analyses were carried out using the ITT population. The primary efficacy endpoint of PFS also was analyzed using the PP population.

The primary analysis was to compare the PFS of subjects dosed with tivozanib with those subjects dosed with sorafenib. The null hypothesis was that the median tivozanib PFS would be equal to that of sorafenib and the alternative hypothesis was that the two PFS medians would not be equal. The IRR was the primary data source for the PFS analysis.

The primary analysis was carried out by using a stratified Log-Rank test, in which the stratification factors were IMDC risk category (favorable; intermediate; poor) and prior therapy (two prior VEGFR TKIs; a prior checkpoint inhibitor (PD-1 or PD1 L inhibitor) plus a prior VEGFR TKI; a prior VEGFR TKI plus any other systemic agent), and using a two-sided 5% significance level. The distribution of the PFS was estimated using the Kaplan-Meier method. The median event time and 2-sided 95% confidence interval for the median was also determined.

i) Analysis of Endpoints: Progression-Free Survival (PFS)

The results for the primary endpoint are shown in FIG. 1, and were determined as follows: after approximately 255 events, defined under RECIST to mean either tumor progression or death, subjects were evaluated for progression-free survival (PFS) by independent radiologic review. Primary analysis performed was by stratified log-rank test. As shown in FIG. 1 and FIG. 6, subjects receiving tivozanib had a median PFS of 5.59 months, compared to a median PFS of 3.88 months for those subjects receiving sorafenib. The stratified log rank probability p-value was 0.0165, indicating a statistically significant difference.

ii) Subgroup Analyses of Progression Free Survival (PFS)

Subgroup analysis of PFS rates were conducted stratified by prior therapy. As shown in FIG. 5, median PFS for the subset of patients receiving a prior check point inhibitor was 7.29 months for the tivozanib arm, whereas the median PFS for the sorafenib arm was only 5.91 months. Additional subgroup analyses of PFS for the ITT population were conducted using a Cox Model as shown in FIG. 10. A forest plot including hazard ratios (HR) with 95% confidence intervals for each subgroup is depicted in FIG. 9. A hazard ratio, including its error range, of less than 1.0 (falling entirely to the left of the vertical dotted line at HR=1.0 in FIG. 9), indicates that treatment with tivozanib demonstrated a statistically significant benefit in PFS compared with treatment with sorafenib. As shown, the hazard ratios for the subgroups of patients receiving prior therapy with two VEGFR TKIs (HR=0.57) or prior therapy with a checkpoint inhibitor plus a VEGFR TKI (HR=0.55) fall entirely to the left of the vertical dotted line, indicating that in these subgroups subjects receiving tivozanib experienced a statistically significant benefit in PFS compared to subjects receiving sorafenib. Further, the hazard ratios for the subgroups of patients with an IMDC Risk Category "Favorable" (HR=0.46) and "Intermediate" (HR=0.69) likewise fell entirely to the left of the vertical dotted, indicating that in these subgroups subjects receiving tivozanib experienced a statistically significant benefit in PFS compared to subjects receiving sorafenib.

The secondary endpoints (OS, ORR, and DoR) were analyzed using the investigator and independent radiological review assessments. The degree of agreement between the investigator and the independent assessment of responses was also determined.

iii) Analysis of Endpoints: Overall Survival (OS)

Figure 2:
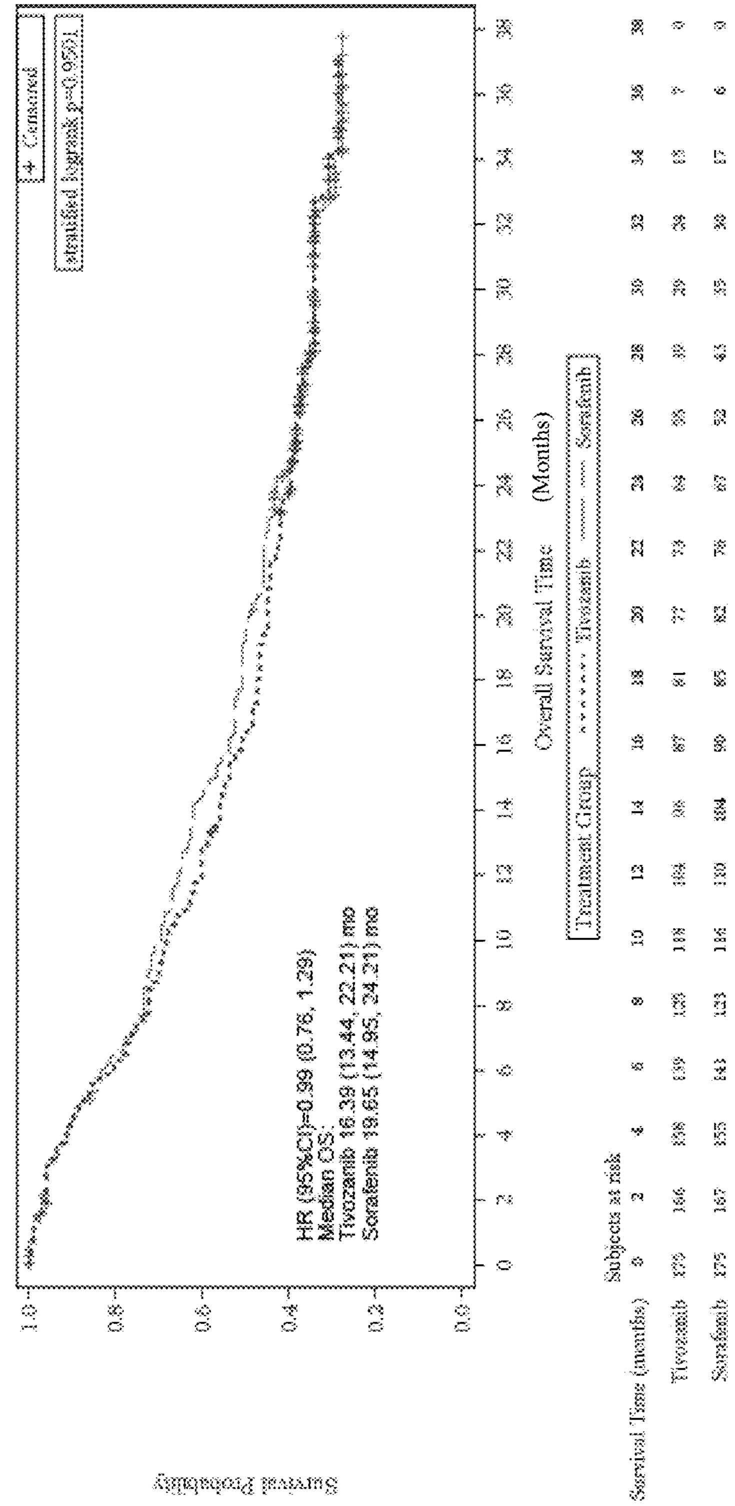
FIG. 2 illustrates the Kaplan-Meier Analysis of overall survival (OS) in months for subjects receiving tivozanib, compared to OS for subjects receiving sorafenib.

An OS analysis was carried out two years after the final patient enrollment. Secondary analysis was performed was by stratified log-rank test. Kaplan-Meier analyses of overall survival are shown in FIGS. 2 and 7, which show that subjects receiving tivozanib had a median OS of 16.39 months, compared to a median OS of 19.65 months for those subjects receiving sorafenib. The HR was 0.99 and the stratified log rank probability p-value was 0.9501. Thus, no statistically significant difference was observed in OS between the two treatment groups.

iv) Subgroup Analysis of Overall Survival

Figure 11:
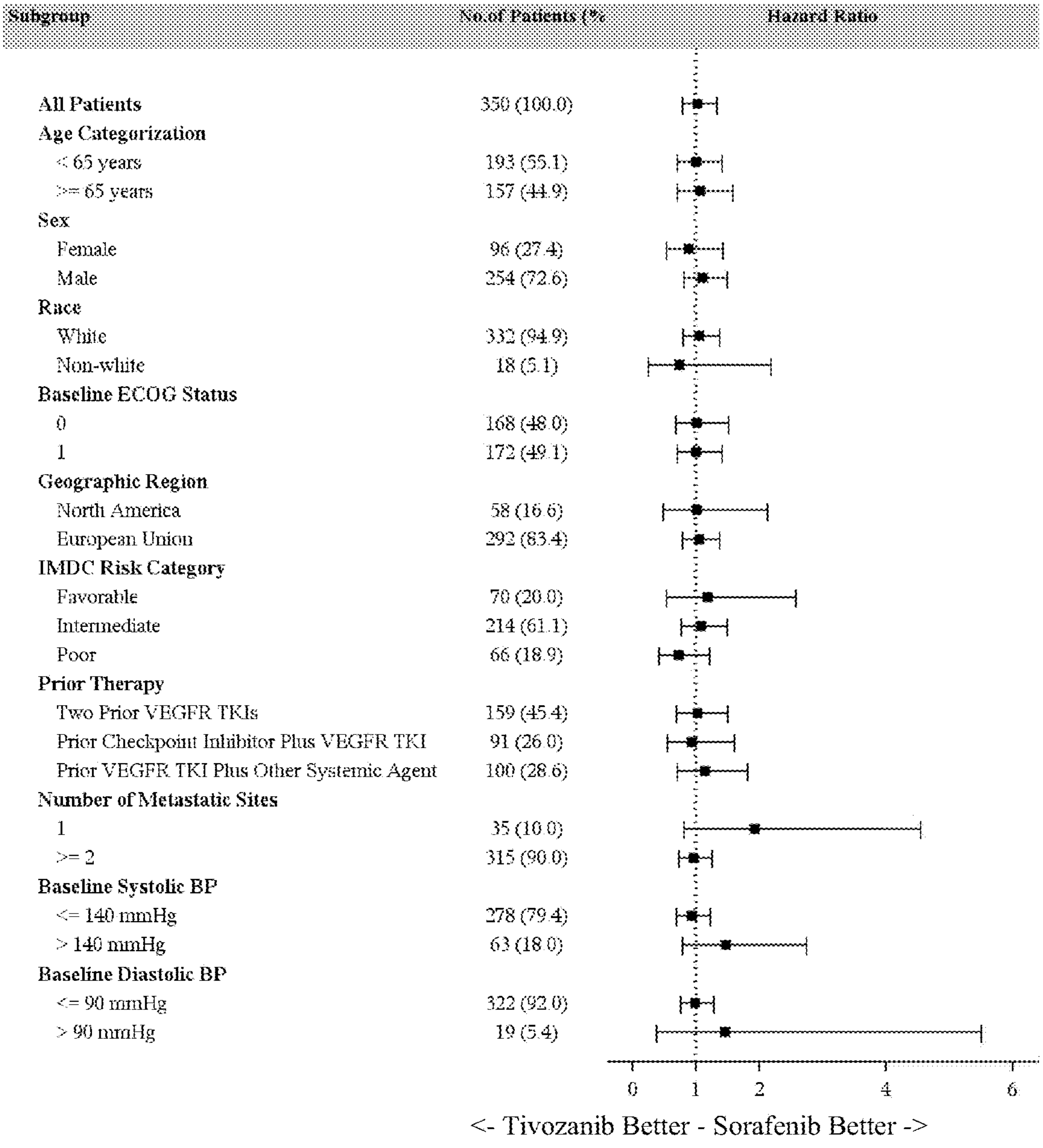
FIG. 11 is a Forest plot of Hazard Ratio with 95% Confidence Interval for Overall Survival (OS) of various patient subgroups.

Additional subgroup analyses of OS for the ITT population were conducted using a Cox Model as shown in FIG. 12. A forest plot including hazard ratios (HR) with 95% confidence intervals for each subgroup is depicted in FIG. 11. The hazard ratios with confidence intervals do not indicate a statistically significant difference in OS between subjects receiving tivozanib or sorafenib. It should be noted, however, that the OS analysis was not controlled for any subsequent therapy after progression.

v) Analysis of Endpoints: Objective Response Rate (ORR)

The proportion of subjects achieving confirmed ORR (complete response [CR]+ partial response [PR]) was summarized by treatment arms and cycle and was compared between the two treatment arms using the Cochran-Mantel-Haenszel (CMH) test with the same stratification factors used for the PFS analysis. As shown in FIG. 3, subjects receiving tivozanib showed an ORR of 18.0 percent (31 PR/172 subjects), compared to an ORR of 8.0 percent (14 PR/175 subjects) for subjects receiving sorafenib.

Analysis of ORR was also conducted for subgroups stratified by prior therapy. As shown in FIG. 12, 79 subjects receiving tivozanib and 80 subjects receiving sorafenib received two prior VEGFR TKI treatments; 47 subjects receiving tivozanib and 44 subjects receiving sorafenib received prior therapy with a checkpoint inhibitor plus a VEGF TKI; and 48 subjects receiving tivozanib and 51 subjects receiving sorafenib received prior therapy with a VEGFR TKI plus any other systemic agent.

The results are shown in FIG. 13, where the data show a trend towards a benefit in ORR for subjects in the tivozanib arm versus subjects in the sorafenib arm in all three subgroups. For subjects who received prior therapy with two VEGFR TKIs, the ORR was 15.2% (12 PR/79 subjects) in the tivozanib arm versus 7.5% (6 PR/80 subjects) in the sorafenib arm. For subjects receiving prior therapy with a checkpoint inhibitor and a prior VEGF TKI, the ORR was 24.4% (11 PR/45 subjects) in the tivozanib arm versus 6.8% (3 PR/44 subjects) in the sorafenib arm. For subjects receiving prior therapy with a VEGFR TKI plus any other systemic agent, the ORR was 16.7% (8 PR/48 subjects) in the tivozanib arm versus 9.8% (5 PR/51 subjects) in the sorafenib arm.

vi) Analysis of Endpoints: Duration of Response (DoR)

The DoR was analyzed using the same method as the progression-free survival analysis. The data are shown in FIG. 14. DoR was only calculated for the subgroup of subjects with an objective tumor response (PR or CR). Thus the sample size for both the tivozanib and sorafenib arms was small. While the results were not statistically significant, in part due to the small sample size, the data show a trend in duration of response favoring tivozanib over sorafenib ($1^{st}$ quartile=9.79 months for tivozanib as compared to $1^{st}$ quartile=5.55 months for sorafenib).

vii) Subjects Treated with Prior Checkpoint Inhibitor: 1-Year Probability of Survival A subset of subjects who had been treated with at least one prior checkpoint inhibitor at any time prior to the study treatment (for example, whether as a first, second, or third line therapy) were also analyzed. For those subjects who received a prior checkpoint inhibitor, a clear difference (unstratified Log-rank p-value=0.0616) was observed in PFS between those subjects who received tivozanib (n=52) and those who received sorafenib (n=46). As shown in FIG. 5, the median PFS for this subset of subjects was 7.29 months for the tivozanib arm as compared to 5.91 months for the sorafenib arm. Further, as shown in FIG. 5, subjects receiving tivozanib after prior anti-cancer therapy with a checkpoint inhibitor were determined to have a 0.37 (~37%) 1-year probability of survival, compared to a 1-year probability of survival of 0.05 (~5%) for subjects receiving sorafenib after prior anti-cancer therapy after prior treatment with a checkpoint inhibitor.

As shown in FIG. 8, no statistically significant differences were observed for OS in this subset between the two treatment groups (unstratified Log-rank p-value=0.8360).

viii) Safety Analyses: Summary of Adverse Events

Additional analyses included the incidence of adverse events emerging during treatment. Not all differences observed between the tivozanib and sorafenib treatment arms were statistically significant. However, as shown in Table 1, subjects in the tivozanib treatment arm exhibited lower incidence of adverse events leading to treatment discontinuation, dose reduction, and dose interruption, as well as lower incidence of treatment emergent adverse events of Grade 3 or higher.

TABLE 1

| | Tivozanib (N = 173) n (%) | Sorafenib (N = 170) n (%) | Total (N = 343) n (%) |
|---|---|---|---|
| Patients with At Least One Treatment-Emergent AE | 171 (98.8) | 170 (100.0) | 341 (99.4) |
| Patients with At Least One Treatment-Emergent AE Leading to Treatment Discontinuation | 36 (20.8) | 50 (29.4) | 86 (25.1) |
| Patients with At Least One Treatment-Emergent AE Leading to Dose Reduction | 41 (23.7) | 65 (38.2) | 106 (30.9) |
| Patients with At Least One Treatment-Emergent AE Leading to Dose Interruption | 83 (48.0) | 107 (62.9) | 190 (55.4) |
| Patients with At Least One Treatment-Emergent SAE | 72 (41.6) | 65 (38.2) | 137 (39.9) |
| Patients with At Least One Treatment-Related Treatment-Emergent AE | 146 (84.4) | 160 (94.1) | 306 (89.2) |
| Patients with At Least one Grade >= 3 Treatment-Emergent AE | 127 (73.4) | 137 (80.6) | 264 (77.0) |
| Patients with At Least one Grade >= 3 Treatment-Related Treatment-Emergent AE | 76 (43.9) | 93 (54.7) | 169 (49.3) |
| Patients with at Least One Treatment-Emergent AE Leading to Death | 16 (9.2) | 13 (7.6) | 29 (8.5) |

Abbreviations:
SAF = Safety;
AE = Adverse Event;
SAE = Serious Adverse Event.

Accordingly, the data suggest that tivozanib is superior to sorafenib in terms of reducing the number of dose reduction, dose interruption, and treatment discontinuation due to adverse events emerging during treatment.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

We claim:

1. A method of treating a subject suffering from refractory advanced renal cell carcinoma, wherein the subject has previously been treated with at least two anti-cancer therapies, wherein one of said anti-cancer therapies is a checkpoint inhibitor, and the other of said at least two anti-cancer therapies is a tyrosine kinase inhibitor, wherein the method comprises orally administering tivozanib to the subject as the only active ingredient to treat the refractory advanced renal cell carcinoma, wherein the tivozanib is part of a pharmaceutical composition consisting of 1.5 mg tivozanib and one or more pharmaceutically acceptable excipients, and the tivozanib is administered according to one or more treatment cycles in which a treatment cycle comprises:

orally administering the tivozanib once daily for 21 days followed by 7 days without administration of tivozanib;

instructing that if a dose of tivozanib is missed by the subject for any reason, the dose is not to be made up; and monitoring for hypertension in the subject, and upon occurrence of hypertension treating the subject with an anti-hypertensive drug prior to any reduction in the dose amount of tivozanib.

2. The method of claim 1, wherein the objective response rate (ORR) in a population of said subjects is at least 100% greater than the baseline ORR of a corresponding population receiving sorafenib.

3. The method of claim 1, wherein the objective response rate (ORR) in a population of said subjects is at least 2.5 times greater than the baseline ORR of a corresponding population receiving sorafenib.

4. The method of claim 1, wherein the 1-year probability of survival in a population of said subjects receiving tivozanib is about 37%.

5. The method of claim 2, wherein the 1-year probability of survival in a population of said subjects receiving tivozanib is about 37%.

6. The method of claim 3, wherein the 1-year probability of survival in a population of said subjects receiving tivozanib is about 37%.

* * * * *